(12) United States Patent
Mc Croskey et al.

(10) Patent No.: US 6,255,655 B1
(45) Date of Patent: *Jul. 3, 2001

(54) GAMMA CAMERA FOR PET AND SPECT STUDIES

(75) Inventors: William K. Mc Croskey, Solon; Christ H. Heipp, Chagrin Falls; David S. Vickers, Independence, all of OH (US)

(73) Assignee: SMV America, Inc., Twinsburg, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/561,719

(22) Filed: May 1, 2000

Related U.S. Application Data

(60) Continuation of application No. 09/152,117, filed on Sep. 14, 1998, now Pat. No. 6,072,177, which is a division of application No. 08/780,647, filed on Jan. 8, 1997, now Pat. No. 5,841,140.

(51) Int. Cl.[7] .................................................. G01T 1/172
(52) U.S. Cl. ................................ 250/363.03; 250/363.04
(58) Field of Search ........................ 250/363.03, 363.04, 250/363.02, 363.09, 252.1

(56) References Cited

U.S. PATENT DOCUMENTS

| | | |
|---|---|---|
| H12 | 1/1986 | Bennett et al. . |
| 4,057,727 | 11/1977 | Muehlehner et al. . |
| 4,395,635 | 7/1983 | Friauf et al. . |

(List continued on next page.)

OTHER PUBLICATIONS

IEEE Transaction on Nuclear Science, vol. NS–23, No. 1, Feb. 1976; "Performance Parameters of a Positron Imaging Camera"; G. Muehllehner, M. P. Buchin, J. H. Dudek; Searle Analytic Inc.; Searle Radiographics Inc., Copyright 1976 by The Institute of Electrical and Electronics Engineers, Inc.

IEEE 1983 Nuclear Science Symposium, Oct. 1983; BNL–33914; "Dual Gated Nuclear Cardiac Images"; I.G. Zubal, Y. Bizais, G.W. Bennett, A.B. Brill; Medical Department, Brookhaven National Laboratory.

1983 Abstract Form for Scientific Papers and Scientific Exhibits; Society of Nuclear Medicine 30th Annual Meeting #BNL–32655; Jun. 7–10, 1983 "Potentiality of D7PHT for Dynamic Tomography"; Y. Bizais, I.G. Zubal, R.W. Rowe, G.W. Bennett, A.B. Brill. Brookhaven National Laboratory.

(List continued on next page.)

Primary Examiner—Georgia Epps
Assistant Examiner—Richard Hanig
(74) Attorney, Agent, or Firm—Frank J. Nawalanic

(57) ABSTRACT

A gamma camera is modified to perform PET studies as well as SPECT studies by utilization of the camera's SPECT electronics to likewise generate triggering pulse signals for photons indicative of a positron annihilation event which are corrected, on a bundled basis, for position, linearity and uniformity by the same digital processors used by the camera for SPECT studies. In addition the triggering pulse signals generate analog timing signals passed through a coarse coincidence circuit to establish matched pairs of timing signals which are digitally time stamped and processed along with the bundled set of pulse signals that the timing signals originated from. The timing signals in turn are corrected from a mapped detector head look up table on the basis of the corrected position of the triggering pulse signal and the time lag between each matched timing signal pair passed through a fine coincidence window processor thus insuring that the line of response passing through the corrected, precisely established positions of scintillations that produced the triggering pulse signals occurred within a time period clearly indicative of a positron annihilation event. By counting only true LORs images having high resolution can be constructed even though the camera's detecting heads cover a limited solid angle of event detections. The timing correction table is generated from an improved calibration technique which factors out those inherent time delays, including signal noise and jitter, which are specific to that gamma camera.

2 Claims, 11 Drawing Sheets

U.S. PATENT DOCUMENTS

| | | |
|---|---|---|
| 4,675,526 | 6/1987 | Rogers et al. . |
| 4,864,140 | 9/1989 | Rogers et al. . |
| 5,023,895 | 6/1991 | McCroskey et al. . |
| 5,241,181 * | 8/1993 | Mertens et al. ................. 250/363.03 |
| 5,272,343 | 12/1993 | Stearns . |
| 5,323,006 | 6/1994 | Thompson et al. . |
| 5,345,082 | 9/1994 | Engdahl et al. . |
| 5,512,755 | 4/1996 | Vickers et al. . |
| 5,532,489 | 7/1996 | Yamashita et al. . |
| 5,585,637 | 12/1996 | Bertelsen et al. . |
| 5,608,221 | 3/1997 | Bertelsen et al. . |

OTHER PUBLICATIONS

"Unicon—A Single Instrument for PET, SPECT, and Routine Clinical Gamma Ray Imaging", G.W. Bennett: A.B. Brill; I.C. Zubal; R.W. Rowe; Y Bizais; R.S. Dobert, Brookhaven National Laboratory, #21.08 (1 page) World Congress on Medical Physics & Biomedical Engineering, 1982, Hamburg.

Reprinted from "Nuclear Instruments & Methods"; A Journal on Accelerators, Instrumentations and Techniques in Nuclear Physics and Related Fields; vol. 192, Nos. 2,3; Feb. 1, 1982; North–Holland Publishing Company–Amsterdam; pp. 491–500.

BNL 32644, Paris FR, Sep. 4, 1982; "Interface Rewquirements in Nuclear Medicine–Devices and Systems", Dept. of Rad., NY Univ Sch of Med; C.O. Maquire Jr., A.B. Brill, M.E. Noz, C.W. Bennett, J.H. Schimpt, S.C. Horil, Y. Yonekura, M.P. Zeleznik, Y. Bizais, B.S. Baxter, I.C. Zubal, L.E. Hitchner.

1982 Nuclear Science Symposium IEEE, Washington, DC Oct. 20–22, 1982 #BNL 32214; "Dual Seven Pinhole Tomography"; Y. Bizais, I.G. Zubal, R.W. Rowe, G.W. Bennett, A.B. Brill.

"Engineering Aspects of a Hybrid Emission Computed Tomograph", M. Tanaka, Y. Hirose, K. Koga, H. Hattori, R/D Engineering Department, Medical Systems Division, Shimadzu Corporation, Kyoto, Japan, Feb. 1981, pp. 137–141.

"Transactions on Nuclear Science", vol. NS–29, No. 1, Feb. 1982 "A Hybrid Emission CT—Heattome II"; Y. Hirose, Y. Ikeda, Y. Higashi, K. Koga, and H. Hattori, R/D Engineering Department, Medical Systems Division, Shimadzu Corporation, Kyoto, Japan; I. Kanno, Y. Miura, S. Miura and K. Uemura, Research Institute of Brain and Blood Vessels, Akita, Japan.

* cited by examiner

GAMMA CAMERA FOR PET AND SPECT STUDIES

This patent application is a continuation of application Ser. No. 09/152,117 filed on Sep. 14, 1998, now U.S. Pat. No. 6,072,177, and incorporated herein by reference, which, in turn, is a division of Ser. No. 08/780,647 filed on Jan. 8, 1997, now U.S. Pat. No. 5,841,140.

This invention relates generally to gamma cameras and more particularly to a gamma camera which is capable of performing both Positron Emission Tomography ("PET") and Single Photon Emission Computed Tomography ("SPECT") studies.

The invention is particularly applicable to and will be described with specific reference to an Anger type camera equipped with two, two dimensional detector heads containing photomultipliers or solid state detectors and NaI crystals capable of performing PET and SPECT studies. However, those skilled in the art will recognize that the invention has applications outside of gamma cameras and can be used in conventional PET ring scanners to improve the accuracy, spatial response and time scans.

INCORPORATION BY REFERENCE

Our application filed as of this date entitled "Prefilter Collimator for PET Gamma Camera" and assigned to the present assignee, SMV America, is incorporated herein. The invention disclosed and claimed herein is believed separate and distinct from that disclosed and claimed in our application filed concurrently herewith.

In addition, the following patents are incorporated by reference herein (as well as documents incorporated or referred to in the patents) so that details known to those skilled in the art need not be restated herein. The documents incorporated by reference herein do not form part of the present invention.

- U.S. Pat. No. 5,532,489 to Yamashita et al., issued Jul. 2, 1996, entitled "Positron Imaging Apparatus";
- U.S. Pat. No. 5,272,343 to Stearns, issued Dec. 21, 1993, entitled "Sorter for Coincidence Timing Calibration in a PET Scanner";
- U.S. Pat. No. 5,241,181 to Mertens et. al., issued Aug. 31, 1993 entitled "Coincidence Detector for a PET Scanner";
- U.S. Pat. No. 5,512, 755 to Vickers et al., issued Apr. 30, 1996, entitled "Gamma Camera Device" and assigned to the assignee of the present invention;
- U.S. Pat. No. 5,345,082 to Engdahl et al., issued Sep. 6, 1994 entitled "Scintillation Camera Utilizing Energy Dependent Linearity Correction";
- U.S. Pat. No. 5,023,895 to McCroskey et al., issued Jun. 11, 1991 entitled "Three Dimensional Tomographic System";
- U.S. Pat. No. 4,864,140 to Rogers et al., issued Sep. 5, 1989 entitled "Coincidence Detection System for Positron Emission Tomography";
- U.S. Pat. No. 5,323,006 to Thompson et al., issued Jun. 21, 1994 entitled "Dedicated Apparatus and Method for Emission Mammography";
- U.S. Pat. No. 4,675,526 to Rogers et. al., issued Jun. 23, 1987 entitled "Method and Apparatus for 3-D Encoding"; and
- U.S. Pat. No. 4,395,635 to Friauf et. al., issued Jul. 26, 1983 entitled "Gamma Ray Coincidence Analysis System".

BACKGROUND

Nuclear or scintillation or gamma cameras are conventionally used to perform SPECT studies. A patient ingests or is injected with a radiopharmaceutical, such as Thallium or Technetium, which emits gamma radiation from a body organ which is the subject of a medical study. The gamma camera detects the radiation and generates data indicative of the position and energy of the radiation which is then mathematically processed through a procedure known as reconstruction tomography (performed by computer) to produce pictures or scintigrams (two and three dimensional) of the body organ which is the subject of the medical study.

A typical gamma camera has at least two detecting heads. Each head contains an array of photomultipliers (PMT) which are arranged behind a scintillation crystal, typically NaI, which in turn is positioned behind a lead collimator. Gamma radiation passing through the collimator strikes the crystal which emits bursts of light or scintillations received by the photomultipliers which in turn generate analog signals indicative of the intensity of the light. The PMT analog signals are grouped, digitized, corrected and processed as data indicative of position, x,y, and intensity, z.

Traditionally, PET scanners are different from gamma cameras. In PET, radio nuclides, typically fluorine-18, carbon-11, nitrogen-13 and oxygen-15 are incorporated into substances such as glucose or carbon dioxide to produce radiopharmaceuticals such as FDG (Fluoro-Deoxy-Glucose) which are ingested by the patient. As the radio nuclides decay, positrons are emitted and they collide, in a very short distance, with an electron and become annihilated and converted into two photons, or gamma rays, traveling linearly in opposite directions to one another with each ray having an energy of 511 Kev. PET scanners typically comprise, laterally spaced rings which encircle the patient. Each ring contains detectors extending thereabout. A typical detector within the ring is a BgO crystal in front of a photomultiplier tube. Each ring is thus able to discern an annihilation event occurring in a single plane. The analog PMT signals are analyzed by coincidence detection circuits to detect coincident or simultaneous signals generated by PMT's on opposite sides of the patient, i.e., opposed detectors on the ring. Specifically, when two opposed detectors detect simultaneous 511 Kev events, a line passing through both detectors establishes a line of response (LOR). By processing a number of LORs indicative of annihilation events an image is reconstructed of the organ using computed tomographic techniques.

Although the literature oftentimes refers to one machine for performing PET and SPECT studies, the radiation events are different resulting in commercially different mechanisms for performing the studies. The PET scanner ring, while one dimensional, forms a complete solid angle about the patient and captures all events in a 2-D slice which can be stacked in accordance with normal tomographic techniques to produce a 3-D image. The gamma camera, while having a 2-D detector head giving it a power factor of one over the scanner ring, can not collect all the positron annihilation events about the patient and in fact, experiences an inherently low count rate which is significantly less than that achieved in a scanner ring. If the gamma camera retains its lead septa collimator (necessary for SPECT studies) photons emitted from non-normal positions of the body can not be accounted for and the low count rate further decreases to the point where the gamma camera simply does not acquire sufficient counts to perform any study with any degree of resolution. For this reason, commercial scanner rings are not fitted with collimators. This particular problem is discussed at some length in U.S. Pat. No. 5,323,006 in which a gamma camera is used to perform PET studies during a mammogram study since the breast can be viewed as being essentially compressed to a two-dimensional object which can be fitted between the detector heads.

Another fundamental problem arises from the different energies of the gamma rays sensed in a SPECT study compared with the significantly higher energy of the PET gamma ray. Thallium doped sodium iodide crystals are conventionally used in gamma cameras for SPECT studies while bismuth germanate crystals are conventionally used in PET scanners. For any given crystal having a given density, crystal thickness is sized to the energy of the ray. BgO crystals are not sufficiently sensitive and are generally unacceptable for SPECT studies. Increasing the thickness of the Nal crystal for positron generated 511 Kev photons will increase the sensitivity of the crystal for PET studies but lead to degradation of the gamma camera when used for SPECT studies. See generally U.S. Pat. No. 4,675,526. A more subtle but significant problem occurs with respect to fluoresence. See U.S. Pat. No. 4,864,140. Using a Nal crystal for PET studies significantly increases the fluorescence problem. Of course this problem is present only if the camera must be used to perform both SPECT and PET studies.

Perhaps one of the most serious problems affecting the commercial feasibility of using a gamma camera to perform both SPECT and PET studies stems from the signal processing capabilities of the camera. As noted above, PET detectors must determine first if a coincident event has occurred and then must determine a line of response for that event and accumulate a sufficient number of LORs to construct an image. Gamma cameras determine an x,y position of an energy ray and attribute an energy level to that position to determine a corresponding pixel definition on a scintigram. While coincident window circuits or electronic collimation to determine the existence of a positron annihilation event are well known, to simply equip a gamma camera with additional hardware and a second digital processing scheme for PET studies will result in a camera significantly more expensive than what can be justified on a commercial basis. The problem is compounded when it is realized that the signal processing scheme must also account for and process angular coincident events because if only photons normal to the detector head are accounted for, the photon count will diminish to an unacceptable level. Thus to adopt into a gamma camera a conventional PET scanner scheme for detecting positron annihilation events in a ring scanner will not necessarily produce the data needed to develop signals resulting from scintillations recorded in the detector heads of a gamma camera.

There are numerous PET scanner coincident detector schemes such as illustrated in U.S. Pat. Nos. 4,395,635; 4,864,140; 5,241,181; and 5,532,489 which determine if two photons struck a detector within a very short time of one another to establish a positron annihilation event. The '181 patent illustrates a conventional arrangement which samples packets of data and processes them through a digital signal processor to determine and identify valid events. The arrangement is sound but the speed of the processing time to determine a scintillation event is not acceptable for a gamma camera modified for PET studies. The '140 and '489 patents use an analogue circuit to determine a coincident event. Generally a triggering signal is developed from a scintillation event and passed with a time delay to an analogue coincident detector circuit which determines within a given time frame whether or not an annihilation event has occurred which is then passed to the digital signal processor for evaluation. In this manner the analogue signal is used to determine whether an event has or has not occurred which is then processed by the slower digital signal processor so that a fast acting coincidence arrangement is produced. This arrangement is also fundamentally sound. As a general concept, the accuracy of the coincident detection circuit is a function of the sophistication and expense of the circuit components so that a "tight" or "fine" detection circuit is obviously more expensive than a "loose" or "coarse" detection circuit.

Gamma cameras use electronics, as a rule, which are not as sophisticated or as expensive as that employed in PET ring scanners. Variations attributed to the gamma camera electronics will typically result in delays which can span anywhere from 30 to 50 nanoseconds for any one camera and not all of that delay can or is attributed to jitter and signal noise. To the extent that the variations can be statistically accounted for through calibration of a gamma camera to produce correction tables, calibration becomes critical to the successful operation of the camera. U.S. Pat. No. 5,272,343 shows an example of a system currently used to calibrate a ring scanner in which a positron source is orbited around the ring to produce better data for calibrating the ring. Such arrangement is not practical or desirable for a gamma camera of the type under discussion.

In the SPECT art it is also known to simultaneously perform imaging utilizing two different radio pharmaceuticals having photons of different energy levels such as technetium and thallium. Within the literature, there is disclosed in U.S. Pat. No. 5,323,006 the concept of performing a breast cancer study using Fluorine-18 in a modified gamma camera followed by placing collimators back onto the camera to thereafter perform a SPECT study. The literature does not disclose performing simultaneously a cancer study using PET images and SPECT images of an organ sequentially taken in one session to generate different images within the same time frame although the medical community could well use such studies in treating the patient.

SUMMARY OF THE INVENTION

Accordingly, it is a principle object of the invention to provide a nuclear camera which can perform both SPECT and PET studies.

This object along with other objects and features of the invention is achieved in a conventional type gamma camera which has first and second detector heads between which a patient is placed and each detector head extends in the x,y directions to span an area. Each detector head conventionally has a scintillation crystal spanning the detector head area and an array of PMTs behind the crystal for generating electrical pulse signals in response to scintillations produced by the crystal from photon interactions, each pulse signal indicative of the intensity of the scintillation in turn correlated to the energy of the gamma ray producing the scintillation. A detecting arrangement is provided which is effective for each PMT when the camera is operated in either a SPECT or PET mode to i) continuously sense, through a sensing mechanism, each PMT's pulse signal to determine when any given pulse signal, a triggering pulse signal, exceeds a preset value, ii) group along with the triggering pulse signal, a plurality of PMT pulse signals which are adjacent the PMT that generated the triggering pulse signal into a bundle of signals, and iii) digitize each pulse signal in each bundled group in an A/D converter to reflect position and energy. The camera is also provided with a coincidence timing mechanism, actuated when the camera is only in a PET study mode, to a) detect through a window timing circuit when any triggering signal from one detector head occurs within a coarse set time period of a triggering signal from the other detector head to establish a matched pair of triggering signals, b) determine, by a time stamping arrangement, a digitized time signal for each of the signals in each matched pair which is indicative of the difference in time of arrival between the triggering signals in each matched pair detected by the window timing circuit and c) gate, through a multiplexor, the bundled PMT pulse signals corresponding to the triggering signals of each matched pair to the A/D converter with the digitized time stamp signals carried therewith while discarding bundled PMT pulse signals having unmatched triggering signals so that in a PET mode, the gamma camera subsequently processes, as digitized signals, only bundled pulse signals which are quickly matched into pairs indicative of a positron annihilation event by analog circuits for a faster more responsive camera. The camera further includes a somewhat conventional digital signal processor enhancement arrangement, effective when the camera is conducting either SPECT or PET studies to i) correct each bundle of digitized PMT pulse signals for linearity, uniformity and energy and ii) establish, by a weighted average of the signals in each bundle, a corrected, x,y triggering signal position at a corrected energy level corresponding to a pixel of a scintigram produced by the camera during SPECT studies or a calculated pair position establishing a LOR when the camera is used in a PET study. Importantly the camera includes a digital synchronization mechanism, operable when the camera is conducting PET studies, to correlate the corrected x,y position signals of each triggering signal including its timing signal into a matched pair to precisely determine a line of response in three dimensional space whereby the apparatus and digital signal processors used in a gamma camera for SPECT studies are fully utilized in the camera for producing improved and enhanced PET studies.

In accordance with an important, significant feature of the invention, the camera further includes a timing correction look up table storing timing data corrections mapped for each detector head and established during camera calibration. The signal enhancement arrangement accesses the look up table for the specific calculated and corrected position of each matched triggering signal to establish a correction value for the timing signal of each triggering signal. The corrected timing signal thus statistically accounts for processing delays inherent in the gamma camera resulting in a timing signal more indicative of the actual time of detection of the photons along a LOR which, as previously noted, has been corrected to define an accurate, pixel location through which the LOR extends. Importantly, a fine coincidence window arrangement is additionally provided where the corrected timing signals in each matched pair of any LOR are checked against a calculated response time for that LOR to insure that the matched triggering signals, now corrected for timing, occur within a fine time span significantly shorter than the coarse time span, and verifying that each matched pair of corrected signals represents a true positron annihilation event.

A significant feature of the invention resides not only in the two step "fast", analog coarse coincidence window followed by a "fine" digital signal processor coincidence window through which timing signals, corrected for processing time delays, must pass but also in the further validation of the timing signals passing through the fine coincident window to insure that the signals used for tomographic reconstruction accurately represent only validated positron annihilation events. Specifically, the invention uses detected Compton scattered rays to establish positron annihilation events so that the count rate of the gamma camera can be increased to offset the prior included angle inherent in the geometry of the gamma camera detector heads. Importantly, a digital signal processor utilizes the corrected energy levels of the scintillations matched to the timing signals which have passed through the fine coincident window to verify that only positron annihilation events are processed by the camera.

In accordance with another separate but significant feature of the invention, the image resolution of the gamma camera is significantly enhanced, by correcting the projection planes formed by the validated timing signals which establish lines of response (LORs) for random events inherent in the PET process and which pass through the fine coincident digital signal processor of the invention. Specifically, the timing signals passing through the coarse coincidence window but rejected by the fine coincident window are not discarded, but instead, histogrammed by a random event digital signal processor which samples the discarded events on a protection by projection, pixel basis which is added, on a plus-minus pixel basis, to the plane projections established by the LORs resulting from the validated timing signals in the framing processor of the invention. In this way the reconstructed images, constructed in a conventional tomographic manner from backprojected planes through which LORs pass, are improved because the backprojected planes, have each been corrected, on a pixel basis, by means of actual recorded data indicative of the random events which must otherwise inherently pass through any coincident window processor.

Yet another important feature of the camera is the provision in the camera of a trigger "jitter" look up table established during calibration to account for inherent initial electronic delays in the gamma camera when initially sensing a pulse signal. The camera further includes a first variable timing delay for one detector head and a second variable timing delay for the other detector head. Software accesses the trigger look up correction table to determine a time lag to impose on the faster acting detector head through its variable delay setting to account for trigger delays inherent in the electronics of the camera whereby the coincidence window circuit, while a coarse discriminator, is nevertheless better able to discriminate matched events from random events because the analog signals have been statistically factored for electronic trigger delay.

In accordance with another specific, important feature of the invention, the camera's sensing arrangement includes a constant fraction discriminator and a zero crossing comparator for generating a triggering timing signal which is processed by the coincidence timing arrangement and corresponds to the triggering pulse signal conventionally detected by the camera. The constant fraction discriminator is actuated by an arming signal in turn developed by the camera's conventional mechanism which detects a triggering pulse signal. Thus, the arming signal actuates the constant fraction discriminator only when the spectral energy of the triggering pulse equals (actually, in practice, slightly less) or exceeds the spectral energy produced by a photon resulting from a positron annihilation so that triggering timing signals are not developed for the typically lower energy SPECT radiation. The detecting mechanism in one embodiment is set to sense positron annihilations which have experienced Compton scattering to increase the count rate of the cameras. In another embodiment, the detecting arrangement is set to a range to prevent arming of the constant fraction discriminator during a SPECT study and permitting the camera to perform dual SPECT and PET imaging in one study.

In accordance with another important, specific feature of the invention, the camera is equipped with a sodium iodide crystals slightly thicker than that customarily used in a gamma camera and each PMT's pulse signal, whether or not a triggering pulse, is sensed by a baseline correction circuit within the camera's pulse sensing arrangement. The baseline correction circuit senses the tail or decay portion of each pulse signal and compares it to the tail or decay portion of the prior pulse signal generated by that specific PMT to obtain a difference signal. The next and entire PMT pulse signal is then adjusted in a summing amplifier by the difference signal to correct for PMT baseline drift on an individual PMT basis. Because the intensity of coincident pair produced scintillations in a NaI crystal of conventional thickness is more intense than conventional PET crystals, fluorescence attributed to the PMT decay portion in the camera is minimized.

An important feature of the invention is the method employed in calibrating the camera for PET imaging to develop correction data which is then used to correct the signals acquired when the camera performs PET scans. The calibration process utilizes the hardware of the gamma camera in a two step process. In the first step a positron emitting radiation point source is placed adjacent the center of, preferably, the center PMT on one detector head. The radiation point source provides a uniform flood of 511 Kev photopeak radiation to all the PMT's of the opposite detector head. The variable delay for the flooded detector head is set at a fast delay of several nanoseconds as is the gating for the coincidence window timing circuit. Timing signals matched from the point source PMT and each pixel of the flooded detector head are obtained and stored in a multi-channel analyzer for each flooded PMT until histograms are developed for each pixel. The histograms which contain spectra of timing data correlated to the pixel areas are sampled and the time delay (including time-of-flight) is factored out of the timing data to build a correction table which is mapped out for the entire flooded detector head. In the second step, the point source is swapped to the other detector head and the process repeated. Finally that histogram for that pixel directly in line with the radiation point source in the first step is compared to that histogram for the pixel (formerly where the point source was positioned in the first step) directly in line with the radiation point source in the second step. Because both LORs are the same, the histograms should, in theory, be identical but in practice, are not. The differences, attributed to triggering jitter or inherent delay in the electronics detecting the initiation of the pulse signals, are calculated and used to adjust the variable delays for the triggering signals in the coincident unit.

It is thus an object of the invention is to provide method and apparatus for conducting PET studies which has improved energy resolution attributed to improved triggering/discrimination of coincident, positron annihilation events.

A more specific object of the invention is to provide for improved, fast, initial detection of positron annihilation events in a PET/SPECT gamma camera by processing analog signal through a "coarse" coincident window followed by digital signal processing of corrected signals through a "fine" coincident window to insure that only coincident pair signals are processed by the camera.

A still more specific object of the invention is to provide, in any camera capable of PET studies, a coincidence window processor capable of determining within a time period of about 10 nanoseconds when a positron annihilation event occurred.

A still more specific object of the invention is to provide a gamma camera capable of PET and SPECT imaging which, because of area detection, results in overall faster scanning studies with less dosages per unit of expensive radioactive isotopes which have to be administered to the patient than that required to obtain a PET scan.

It is an object of the invention to provide method and apparatus which enables a gamma camera to use its conventional SPECT digital signal processors and data collection circuits to provide weighted and corrected position signals through which a LOR extends when the gamma camera is used to perform PET studies whereby accurate positions of positron annihilation events can be developed.

In accordance with the immediately preceding object of the invention, it is yet another specific object of the invention to utilize the gamma camera's conventional PMT pulse signal processing arrangement to develop timing signals from timing circuits which are subsequently processed with conventional gamma camera data to insure coincidence pair matching and validated positron annihilation events whereby the gamma camera is able to perform PET studies.

A more general object of the invention is to provide a PET system which when compared to conventional systems has improved:

i) spatial resolution in that it can image smaller size articles ii) in a shorter overall scan time iii) with a lower radiation dose.

A still further object of the invention is to provide a dual SPECT/PET system which can be sequentially operated or multiplexed during a single scan to perform dual PET and SPECT imaging studies useful in certain cancer studies.

An important object of the invention is to provide a gamma camera which, when operating in its PET mode, reduces the probability of processing single radiation events, or random events, as true positron annihilation events.

In connection with the foregoing object, it is another important object of the invention to provide a gamma camera which can perform PET studies, despite its inherently poor solid angle limiting the camera's ability to detect the occurrence of all coincident pair events, because the camera's probability of processing only true positron annihilation events has been increased to the point where images can be reconstructed from a relatively small data sampling.

An important object of the invention is to modify a gamma camera for PET studies in which scintillation signals indicative of a positron annihilation event are rapidly processed through a coarse coincidence window after which the signals, indicative of positron annihilation events, are corrected by several unique signal processors, and passed through a fine digital signal coincidence window processor, so that the gamma camera processes only corrected signals occurring within a short time span of one another indicative of only true positron annihilation events.

In accordance with the immediately preceding object of the invention, a still further object of the invention is the provision of a random event digital signal processor which uses actual data acquired during the PET scan to modify the plane projections established by a digital framing processor to account for random events inherently passing through the fine digital signal window processor and to significantly improve the image resolution capabilities of the gamma camera.

A still further object of the invention is to provide a gamma camera operable in a PET mode to process a high count of positron annihilation events by accurately matching gamma radiation having spectral photopeak energies of about 511 Kev with coincident pair gamma rays which have experienced attenuation attributed to Compton scattering.

Another important object of the invention is to provide a gamma camera capable of performing SPECT and PET studies which automatically corrects for baseline drift including fluorescence attributed to the pulse decay in a PET study.

A further significant object of the invention is to provide a new method of calibrating a camera for PET studies which produces accurate time correction factors for that specific camera to permit the camera to sense positron annihilation events with a higher degree of accuracy than heretofore possible.

Still another object is to provide a method of time calibrating any nuclear camera, including conventional PET ring scanners, which is relatively fast and easy to perform and which corrects for delays in the initiation of the camera's detectors separate and apart from the delays attributed to the camera's processing of detected signals.

Still another important object of the invention is to provide a gamma camera which fully utilizes the camera's processors and electronics necessary to perform SPECT studies to generate improved signals which make the camera, with a minimal addition of new components, capable of performing PET studies.

Still another specific object of the invention is to provide a gamma camera capable of performing both SPECT and PET studies which utilizes software generated information, specific to each camera, in its hardware to produce high quality images thus avoiding expensive and complicated hardware system otherwise required to produce the images.

Yet another object of the invention is to provide a gamma camera capable of performing SPECT and PET studies at a cost significantly less than conventional ring type PET scanners.

These and other objects of the invention will become apparent to those skilled in the art upon reading and understanding the Detailed Description of the Invention set forth below taken in conjunction with the drawings.

BRIEF DESCRIPTION OF THE DRAWINGS

The invention may take form in certain parts and in an arrangement of certain parts taken together and in conjunction with the attached drawings which form part of the invention and wherein.

DETAILED DESCRIPTION OF THE INVENTION

Figure 1:
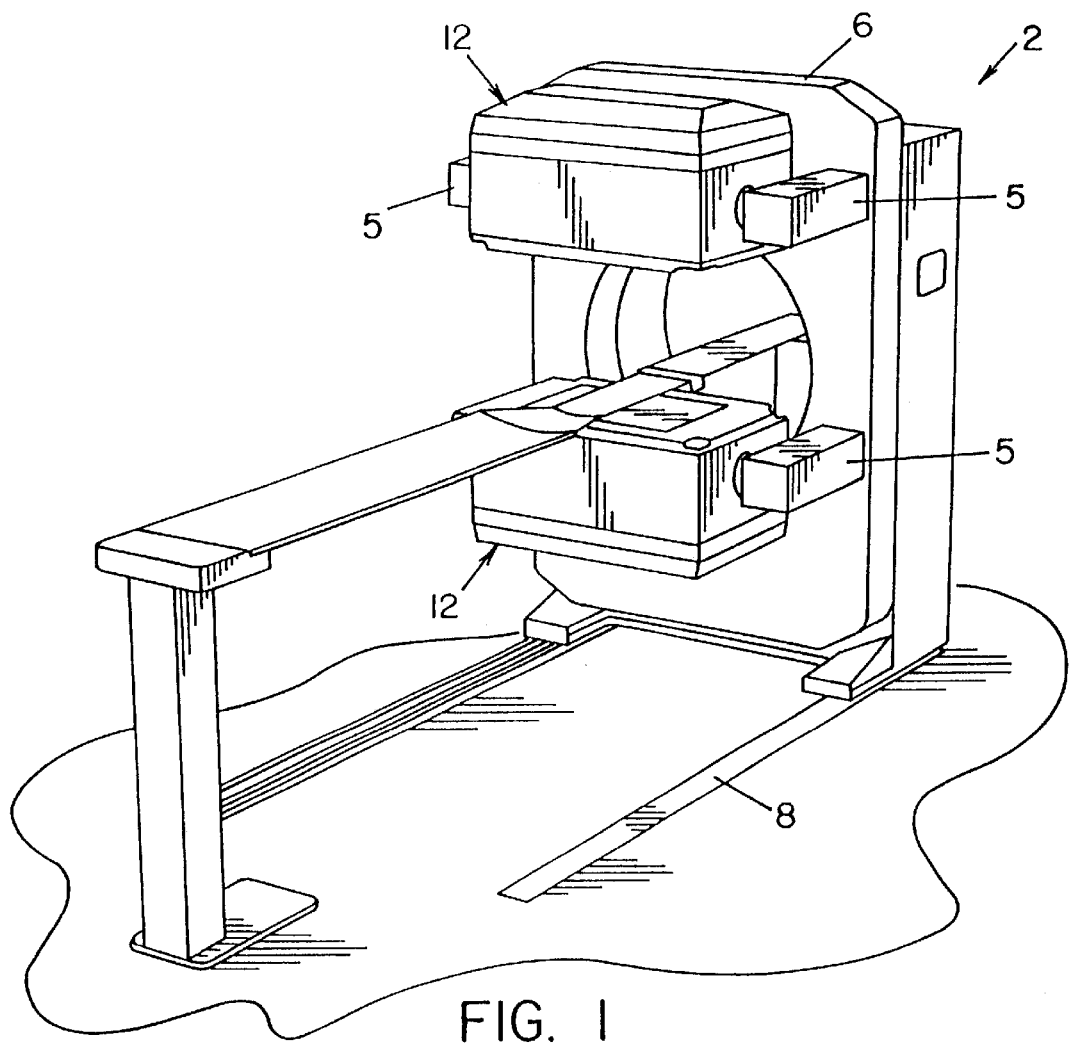
FIG. 1 is a pictorial view of a gamma camera.

Referring now to the drawings wherein the showings are for the purpose of illustrating a preferred embodiment of the invention only and not for the purpose of limiting same, there is shown in FIG. 1 a gamma camera 2 having two detector heads 12 between which a patient is situated. (Two detector heads are shown in the preferred embodiment but those skilled in the art will recognize that the camera could employ 3 or 4 detector heads. While multiple heads will increase the count rate, the camera has been found to adequately function with two heads.)

Detector heads 12 are mounted on arms 5 to a conventional gantry arrangement 6 which permits detector heads 12 to be positioned about the patient in any angular arrangement relative one another and at any distance between one another. Those skilled in the art will recognize that when the camera is in operation, especially for PET scans, the mechanisms conventionally employed in the camera by the technician to adjust detector heads 12 also records the distance between detector heads 12 which information is used when correction look up tables are employed to modify the signals obtained from detector heads 12. Imaging is performed in a conventional manner with the patient stationary. Detector heads 12 are positioned about patient 10 at a fixed distance sufficient to obtain satisfactory image resolution. The heads can then rotate about the patient to take additional images or move on a gantry track 8 to other longitudinal positions of the patient for imaging other organs of the patient. In PET studies, the area of the detector heads in a gamma camera minimize such longitudinal movements when contrasted to the numerous longitudinal ring positions required by PET ring scanners to perform a PET scan. The invention, for reasons discussed below, is able to acquire PET images of that portion of the body organ contained within the x-y area of detector heads 12 in one scan. Although the gamma camera PET scan may be longer than a scan performed by a ring in PET ring scanner because only one scan has to be taken, the overall scanning time is materially reduced by the invention's gamma camera.

Figure 2:
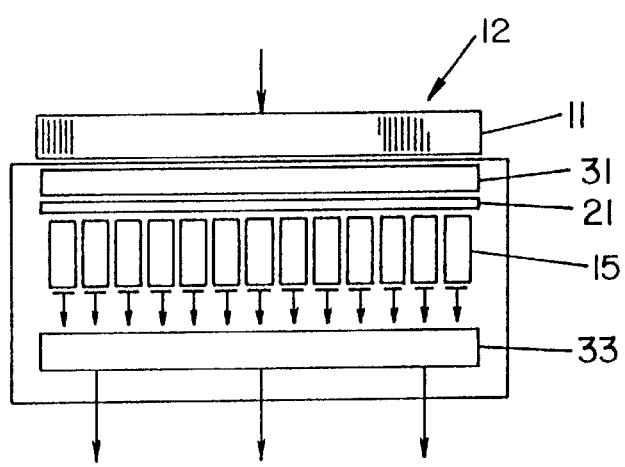
FIG. 2 is a schematic representation of the physical components of the detector head of a gamma camera.

Referring to FIG. 2, each detector head 12 includes a removable collimator 11 behind which a thallium doped sodium iodide crystal 31 is positioned. Light guides 21 are positioned behind crystal 31 for guiding scintillations from crystal 31 normal to the face plates of photomultipliers or PMTs 15. PMTs 15 are mounted in an array (58 PMTs in the preferred embodiment) extending in the x-y direction over a discrete area. PMTs develop analog pulse signals and reference can be had to the assignee's prior U.S. Pat. No. 5,512,755 for a more detailed description of how the analog signals are developed and refined in each PMT 15 than that which will be explained herein. The electrical pulse signals are then processed by a conventional processor 33. As will be explained later, gamma camera 2 is operated in a SPECT mode with collimator 11 in place. When gamma camera is operated in a PET mode. Collimator 11 can be either removed, or removed and replaced with a filter plate or left in place. Specifically, if the collimator is a "thin" collimator, camera 2 is conducting both PET and SPECT studies at the same time a thin collimator is fitted to each detector head 12. Generally speaking, gamma radiation produced in SPECT studies is at a lower spectral energy than that radiation produced in PET studies. The thickness or channel depth of collimator 11 is sized relative to the spectral energy of the isotope used for any specific SPECT study. Collimator thickness increases as spectral energy of the radiation increases. It is customary in the trade to supply gamma cameras with three different collimator thicknesses, "thick", "thin" and "medium", to cover the spectral energy range of the gamma rays produced in SPECT studies.

Figure 3:
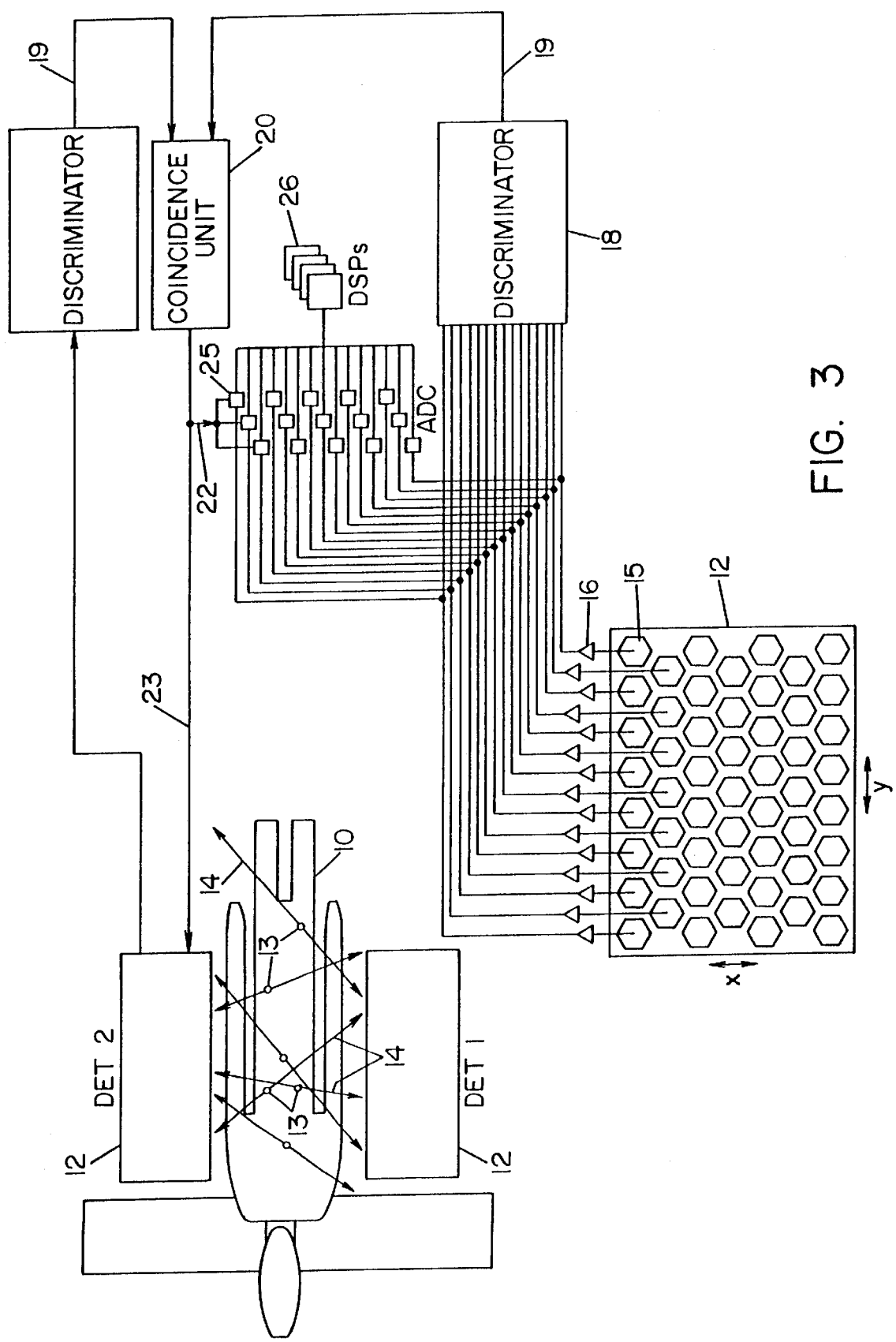
FIG. 3 is a general pictorial/schematic illustration of the detector portion of the camera of the present invention operating in a PET mode.

Referring now to FIG. 3, a patient 10 has ingested (or been injected with) a radio pharmaceutical such as FDG which, upon decay, and as discussed above, produces positron annihilations shown as points indicated by reference numeral 13 in FIG. 3. Those skilled in the art know that each positron annihilation 13 or "event" produces two photons or gamma rays having energy of 511 KeV traveling in opposite directions in a straight line along a line of response (LOR) indicated by reference numeral 14. Photons travel at the speed of light (approximately 12 inches in one nanosecond). It is thus possible to determine the time it takes for a photon to travel a straight line (LOR) from any point on one detector head to any point on the confronting detector head, which for convenience will be designated the base time Tb. The positron annihilation event 13 occurs at some position on LOR 14 and two photons travel, in opposite directions, at the speed of light from the positron annihilation event to strike the confronting detector heads 12. The actual time, Ta, from the instant the first to arrive photon strikes one detector head to the instant the later arriving photon strikes the opposite detector head then is always less than the base time Tb, up to a maximum of ½ Tb when the positron annihilation event 13 occurs at the precise midpoint of the LOR. It is thus possible by comparing Ta to Tb to first determine whether the two events could even be a coincident pair (i.e., Ta>Tb) and second, to theoretically determine two positions on each LOR where a positron annihilation event 13 occurred. As explained below, the invention utilizes this concept by time stamping each photon event from a positron annihilation. Specifically the photon which is the first in time to strike a detector head 12 is given a zero time stamp so that the later arriving time stamp is effectively time stamped with a value indicative of Ta. Of course, commercial electronics and digital signal processors inherently have time delays which far exceed the time-of-flight nanosecond fractions theoretically required to determine if a coincident event occurred, let alone determine the position on a LOR where a positron annihilation event 13 occurred. What is universally done is to take a large number of LOR samples which are histogrammed and statistically analyzed. Depending on the tomographic techniques employed, PET images, in theory, can be evolved either from a large number of LORs or from a smaller number of LORs also containing data indicative of possible positions on the LORs where an annihilation event occurred. In theory, so long as the sample size is large enough, any reasonably accurate timing arrangement can be utilized since variations in the coincident measurements can be statistically factored from a large data population. However, when two detector heads similar to that used in a gamma camera are fitted with coincidence window detecting circuits for establishing the LORs used in a PET study, the solid angle through which data can be collected is materially reduced when compared to that generated by the rings of conventional PET scanners and the count rate significantly drops. Inherently, the gamma camera cannot produce for any one dimensioned slice through the object within any reasonable time a sample size of annihilation events equivalent to that produced by a PET ring scanner. It is therefore extremely important, for image resolution and clarity and for the gamma camera to even produce a picture, that the maximum possible number of true positron annihilation events be sampled while discarding all single or random events from the data so that the relatively small sample size collected (compared to that of a PET ring scanner) is distorted as little as possible. Accordingly, one of the underpinnings of the invention then is to arrive at method and apparatus which provide corrections to the signals and those corrections, in turn, are based on data acquired for that specific camera which can be statistically sampled in a reliable manner. When the correction factors used in the invention are applied to the data acquired by the gamma camera, a remarkable high incidence rate of true positron annihilation events are processed with only a relatively small number of random events. Those skilled in the art will also recognize that while the method and apparatus disclosed herein are disclosed for specific application to a gamma camera, the concepts are likewise applicable to PET ring scanners.

FIG. 3 generally illustrates the overall processing scheme when the gamma camera is operating in its PET mode. Each PMT signal is amplified through its PMT preamplifier circuit board 16 and is then passed through a discriminator unit 18 which determines if any PMT pulse signal had achieved an intensity or voltage indicative of a positron annihilation event 13 and, if so, transmits a triggering signal 19 corresponding to the detected PMT pulse signal to a coincidence unit 20. Coincidence unit 20 determines whether or not any two triggering signals 19 from opposite heads occurred within a given time of one another and, if so, the triggering signals are utilized to effect further processing of the associated PMT signals. More specifically, each triggering signal, i.e., each matched pair, is passed back, indicated by reference numeral 23, to its respective detector head 12 to allow or gate PMT signals associated with the triggering PMT as well as the triggering PMT to be further processed. Each triggering signal in a matched coincident pair is also further refined into a timing signal shown by reference numeral 22 which is digitized and combined with the gated PMT signals which are also digitized in analog to digital converters 25. The PMT signals which have now been time stamped are then processed through digital signal processors 26 to develop data subsequently used to produce tomographic images.

For consistency in terminology, a PMT produces an electrical signal having a voltage corresponding to the intensity of the light produced in the crystal from a photon interaction. Since photons produce scintillations or bursts of light, the PMT's electrical signal will correspond to a voltage/time pulse or photopeak curve in turn directly correlated to the scintillation in turn directly correlated to the energy of the photon which in turn is established by the specific radioisotope ingested by the patient. Thus PMTs produce a string of pulse signals. The pulse signals in turn are analyzed. When a PMT pulse signal is integrated, a value corresponding to the energy of the scintillation is produced and when the pulse amplitude exceeds a preset value corresponding to the particular gamma radiation under study, it is assumed that a gamma ray impacted the crystal in front of that PMT. Thus when the amplitude of the pulse signal exceeds a preset value, the specific PMT which generated that pulse signal is termed a "triggering PMT" and the PMT signal is deemed a "triggering pulse signal" indicative of a scintillation caused by a photon interaction in the crystal or a scintillation event. In this invention, the triggering pulse signal along with a bundle of adjacent or related pulse signals are integrated and processed as a group to achieve weighted signals. When the invention is used as a PET scanner the triggering pulse signal is also used to generate a timing signal which is referred to as triggering timing signal (although shorthand notation may refer to "triggering signal" to designate either triggering pulse signal or triggering timing signal since both signals are based on the same PMT pulse signal). When coincidence unit 20 detects coincident triggering timing signals from both detector heads, a matched pair of triggering timing signals (which correspond to a matched pair of triggering pulse signals or, in shorthand notation, a matched pair of triggering signals) indicative of a positron annihilation event is detected and each triggering timing signal of the matched pair is digitized and time stamped to become a time stamped signal. The two time stamped signals of the matched pair of triggering time signals thus establish a time difference or delta time or time lag correlated to the time difference between the time that the first in time positron annihilation photon struck the crystal on one detector head and the time the second in time positron annihilation photon struck the crystal on the opposite detector head.

Figure 4:
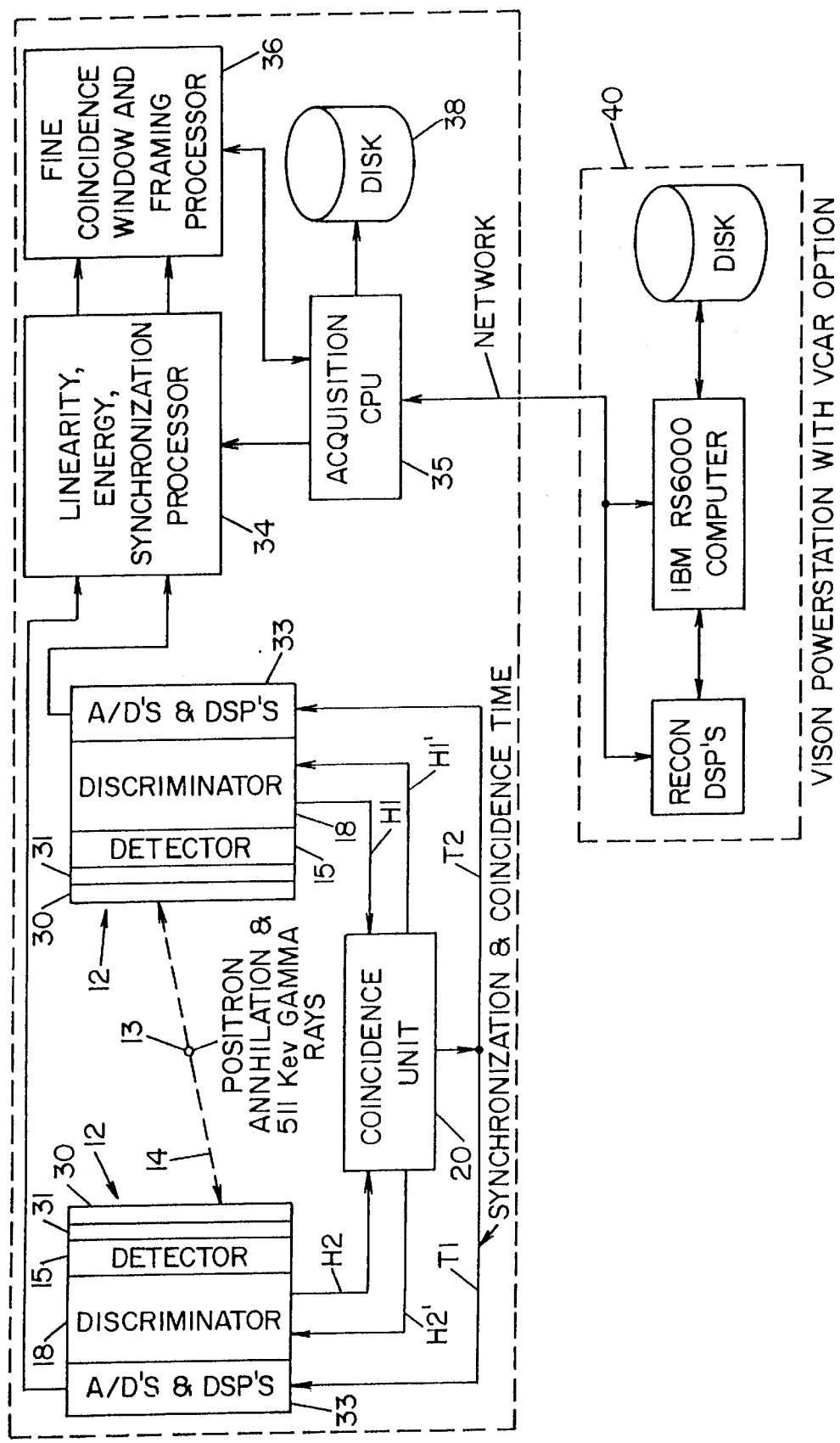
FIG. 4 is a general schematic arrangement showing the principal components, in block form, of the gamma camera of the present invention.

FIG. 4 illustrates the overall general processing scheme in greater detail than FIG. 1. In one embodiment, each detector 12 is not collimated and simply has a plate covering a sodium iodide crystal 31 which in the preferred embodiment is about ½" thick. Scintillation crystals in gamma cameras are almost universally thallium doped sodium iodide crystals typically ⅜" thick which have been found to produce scintillations for gamma radiation generated by radioisotopes such as technetium, thallium, etc. falling within a responsive or idealized band width range of conventional PMTs. The thickness of the crystal used in the invention is increased to about ½" (practically, sodium iodide crystal thicknesses of ½" to ¾" will function acceptably) to absorb a higher percentage of scintillations corresponding to positron annihilation photons of 511 Kev for PET studies while also being able to cause scintillations for the lower energy photons produced during SPECT studies without experiencing image degradation.

As is well known, when the energy of photon is absorbed in a crystal, a scintillation is produced by that crystal. For a crystal of any given density a percentage of photons of any given radiation will be absorbed at various depths of the crystal with some percentage of the photons passing through the crystal. As the spectral energy of the radiation increases, a higher percentage of photons will pass through the crystal without absorption. Increasing the thickness of the crystal will result in higher percentages of photon absorption. However, at lower energy rays, the depth in the crystal where absorption occurs becomes further removed from the light tubes which carry the scintillation to the PMTs and tends to introduce errors because the light beams fan out, etc. Thus, simply increasing the thickness of a crystal to absorb a higher percentage of the coincident pair radiation will result in degradation of the images when the camera is used to image the spectrally lower energy radiation typically encountered in SPECT studies. The obvious solution then is to increase the density of the crystal and PET scanners typically use a bismuth germanate crystal for this reason. However, a bismuth germanate crystal will produce less intense scintillations for the lower energy SPECT study radiation and, in fact, the scintillations will fall outside the preferred response range of the PMTs. For this reason, a thallium doped sodium iodide crystal is used in the present invention with a thickness only slightly greater than that typically used in conventional gamma cameras designed only to conduct SPECT studies. In this regard, several points are to be noted. First, a prefilter plate is used over the crystal and is described in our co-pending application, filed as of this date, entitled "Prefilter Collimator for PET Gamma Camera" and assigned to the current assignee, SMV America. Second, without a filter plate a relatively higher percentage of radiation producing 511 Kev photopeak will pass through the NaI crystal, but a significant percentage of that radiation will be absorbed so that when Compton scattered scintillations are counted along with the 511 Kev scintillations, the camera can function to produce images. Third, when the camera is used to conduct dual PET and SPECT studies, a "thin" lead collimator is used in place of the filter. A significant portion of the 511 Kev radiation will pass through the collimator and be detected, although at an attenuated value, by the camera. At the same time, the collimator will detect lower energy radiation in the normal manner for SPECT studies. Therefor, in this invention, a filter plate is not necessarily used with the camera, and a thin collimator is used with the camera when the camera is performing dual SPECT and PET studies. For definitional purposes, a "thin" collimator is one having a septa thickness between channels which will permit more than about 50% of 511 Kev coincident pair radiation to pass through the septa with Compton scattered attenuation at levels high enough to be detected by event detector 52, i.e., about 200–250 Kev. At the same time, the "thin" collimator will "stop" high angle 511 Kev Compton scattered radiation produced in the body organ preventing erroneous LORs (low angular Compton scattered deflection passing through the thin collimator will adversely affect the LOR).

Scintillations from crystal 31 are transmitted through light guides 21 to the face plate of PMTs 15 which in turn develop analog pulse signals indicative of the intensity of the scintillations. Those pulse signals, if indicative of an annihilation event, become triggering pulse signals which generate triggering timing signals for each detector head 12, designated H1 and H2, respectively, in FIG. 4. Coincidence unit 20 determines for any one H1 or H2 triggering signal received if a second triggering signal H2 or H1 has occurred from opposite detector head 12 within a given time span. If two signals "match" those matched triggering timing signals, now H1' and H2' are sent back to their respective detector heads 12 for gating the triggering pulse signal and a preset plurality of adjacent pulse signals which have been bundled together to permit further processing of the scintillation pulse signals corresponding to matched triggering timing signals H1' and H2'. If a matched triggering timing signal set is not observed within the coincidence time, then that triggering timing signal H1 or H2 which was initially sent to coincidence timing unit 20 is discarded and the bundled scintillation pulse signals for that specific triggering timing signal H1 or H2 are also simply discarded. Coincidence unit 20 thus sequentially processes the triggering timing signals on a first in time basis. The first in time triggering timing signal, say H1, becomes the reference signal and the first in time signal from the opposite detector head H2 is checked against H1 for coincidence. If coincidence is detected, the signals are matched or paired and processed as a matched set. If coincidence did not occur, H1 is discarded and H2 becomes the reference signal against which the first in time signal from now the opposite detector head H1 is compared. In this way coincidence timing unit 20 provides a fast acting and responsive timing mechanism which matches up and initially makes a coarse determination whether or not a positron annihilation event has occurred thus reducing the adverse pile up effects attributed to multiple scintillations discussed above. Only events which are likely to eventually be determined as valid positron annihilation events and not random events are processed by the significantly slower acting digital signal processors utilized in gamma cameras.

Coincidence unit 20 also acts to generate a timing signal for each matched pair of triggering timing signals H1' and H2'. The timing signals designated as T1 and T2 in FIG. 4 are digitized and sent to the conventional analog to digital converters and digital signal processors used on gamma cameras indicated generally by reference numeral 33 in FIG. 4. More specifically, in the preferred embodiment, timing signals T1 and T2 are digitized into four, 8 bit signals. One of the 8 bit digitized signals contains timing data and the other three 8 bit digitized signals contain 24 bits of synchronizing information, correlating H1' and H2' and their respective bundled signals with one another after processing through conventional digital signal processors 33. Utilization of the conventional processing scheme of the gamma camera for PET studies is one of the underpinnings of the invention. More specifically it was determined that good resolution PET scanner images could be obtained using the conventional bundling and processing correction scheme of the gamma camera with the only modification being the addition of a time stamp digitized piece of information added to the digitized PMT pulse signals normally developed by the gamma camera in a SPECT mode.

Referring still to FIG. 4, once the PMT pulse signals have been bundled, time stamped and gated, the conventional gamma camera signal processors 33 sends the digitized, time stamped bundles of PMT pulse signals to signal enhancement digital signal processors 34 under the control of a data acquisition CPU 35. Signal enhancement processors 34 perform the conventional linearity and energy signal corrections commonly employed in SPECT studies. For example, see U.S. Pat. No. 5,345,082. In addition, for PET imaging, enhancement processors 34 synchronize the matched signal and transmit the signals to fine coincidence and framing digital signal processors 36 also under the control of data acquisition CPU 35. Fine coincidence processors 36 determine through correction look up tables which of the matched signal events are valid positron annihilation events and the refined signals and computed LORs can be stored on disk 38 for later reconstruction in tomographic station 40 or alternatively, the signals can pass immediately to tomographic station 40. When the camera is used for SPECT studies, the signals simply pass through signal enhancement processors 34 for conventional storage onto disk 38 for scintigram construction. Thus the conventional SPECT imaging scheme is utilized in the PET studies of the gamma camera obviating the need to construct entirely different processing schemes and minimizing the cost of the camera while resulting in good resolution images in both SPECT and PET imaging modes.

Figure 5:
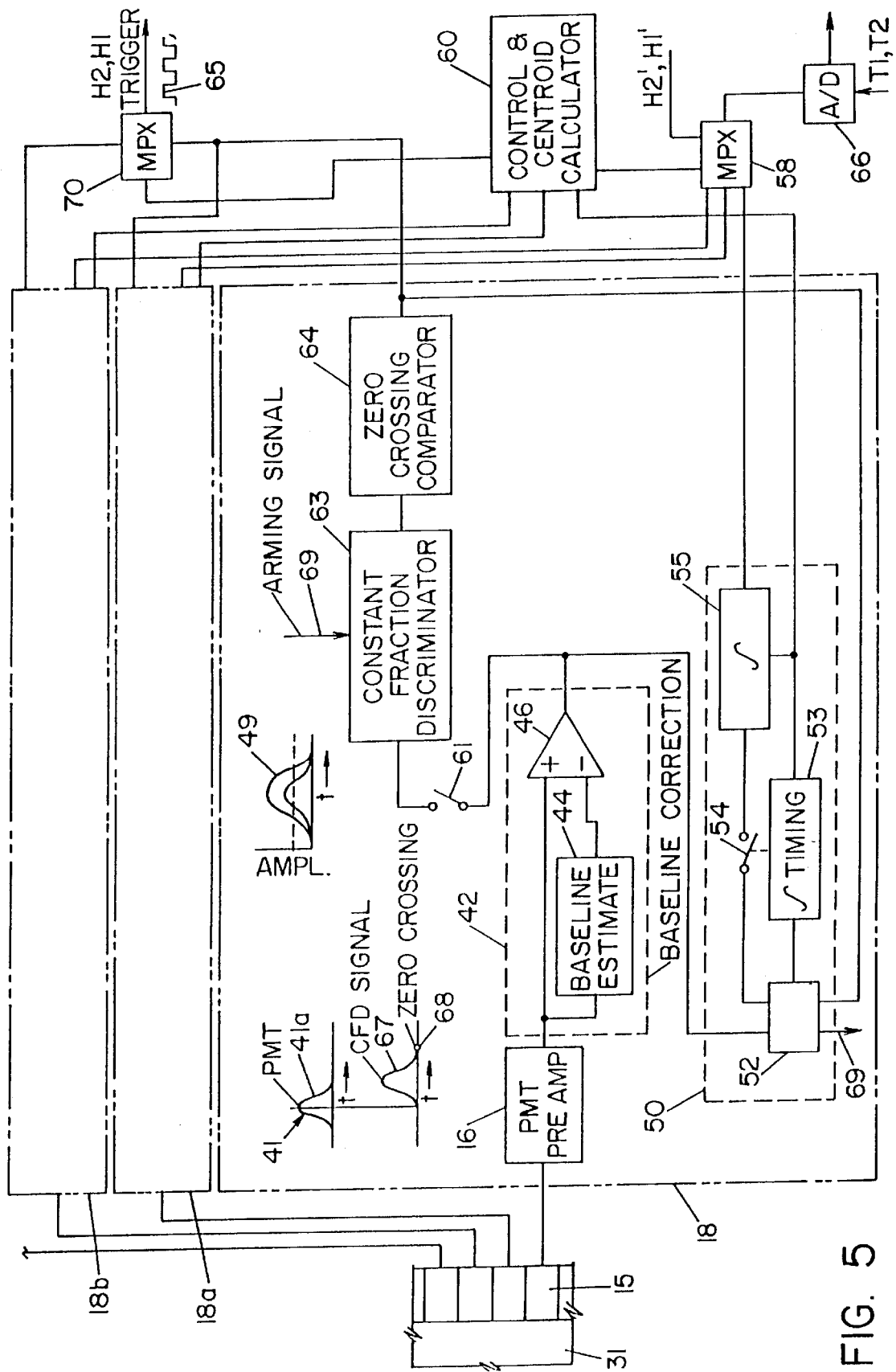
FIG. 5 is a general schematic, block diagram of a portion of the PMT signal processor which develops the trigger signal used in the coincidence timing circuit of the invention.

Referring now to FIG. 5 the general arrangement for developing triggering timing signals H1 and H2 is generally shown. It is to be noted that all specific, individual components discussed herein in connection with the gamma camera are per se well known in the art and do not, in and of themselves, form part of the present invention and thus will not be described or illustrated in detail herein. As noted above in the preferred embodiment there are 58 PMT's 15 in each detector head 12. Each PMT is fitted with a divider board, a gain board and a preamp board as described in SMV's U.S. Pat. No. 5,512,755 incorporated herein by reference. Each PMT is also provided with a discriminator unit as shown by the dot-dash envelopes 18, 18a, 18b etc., of FIG. 5, there being 58 discriminators 18 per each detector head 12. For illustrative purposes only, the PMT's preamp circuit board 16 is shown within the envelope of discriminator 18.

Figure 6:
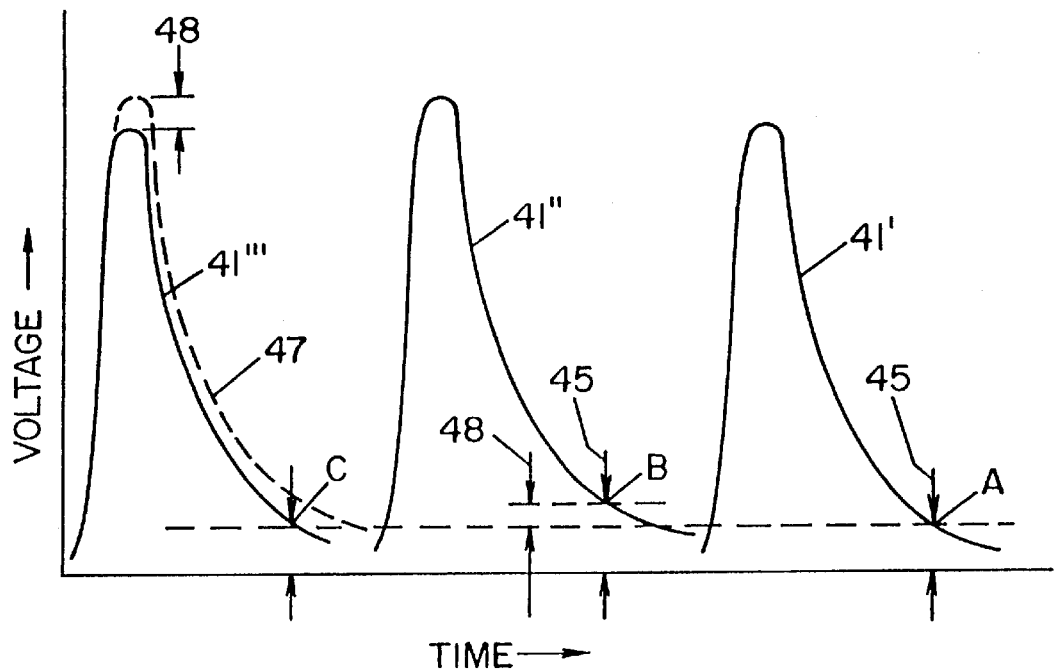
FIG. 6 is a graph showing a series of photopeak or pulse signals produced by the PMT's of the gamma camera.

Each PMT's pulse signal, indicated graphically by curve 41, passes through a baseline correction circuit indicated by dash line envelope 42 where it is corrected for drift. Those skilled in the art know that the camera will drift over time. As best shown in FIG. 6, each pulse signal 41 characteristically has a tail portion 41a which gradually will reduce to zero voltage. Over time, the tail will drift from zero. Baseline correction circuit 42 measures the voltage of the tail of each pulse. The tail voltage sensed for any given pulse is compared to the tail voltage sensed for the immediately preceding pulse to obtain a difference signal and that difference signal is then used to adjust the pulse voltage of the next successive pulse accordingly. The correction essentially establishes a hunting action which, over several cycles, quickly nulls to a stable correction. As diagrammatically illustrated in FIG. 6, a first pulse signal 41' is measured, for illustrative purposes, at a tail position 45 and produces voltage signal A. The next successive pulse 41" measured at tail portion 45, produces tail voltage reading B so that A–B establishes a difference signal equal to voltage difference 48. The next successive pulse 41'" is adjusted by voltage difference 48. Without the adjustment, pulse 41'" would assume the shape of dashed curve 47.

Figure 6A:
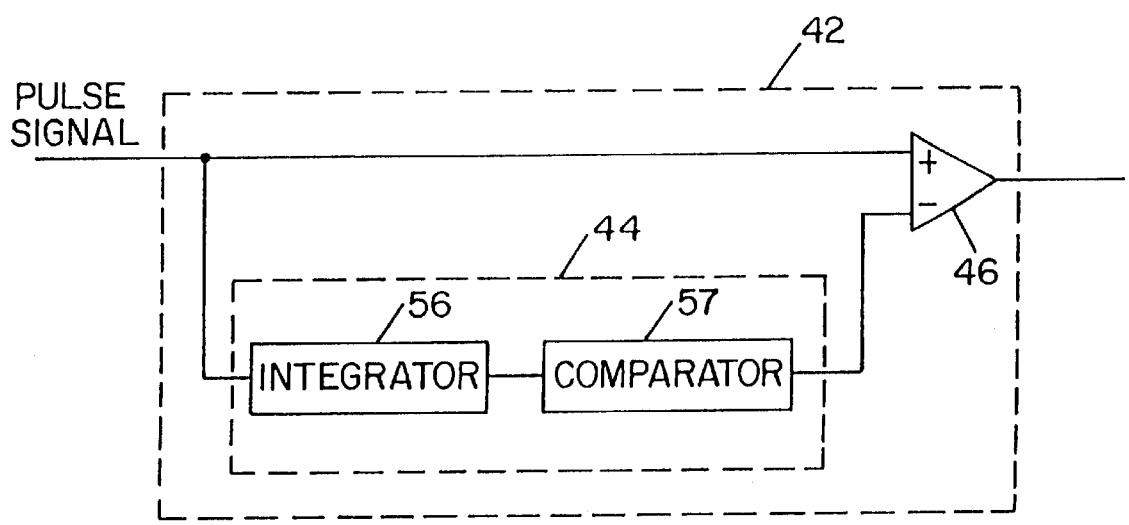
FIG. 6a is a schematic of a baseline correction circuit used in the invention based on the technique illustrated in FIG. 6.

Any number of circuits can be readily constructed to accomplish the correction diagramed in FIG. 6. One type of baseline correction circuit 42 is generally illustrated in FIG. 6A and includes a conventional integrator 56 (typically employed in gamma cameras) for integrating the pulse curve over its tail portion, a comparator 57 for comparing the current pulse tail integrated area with the immediately preceding pulse's tail area and generating a difference signal which is then summed or subtracted in a summing amplifier 46. Other arrangements will suggest themselves to those skilled in the art.

As discussed above, a sodium iodide crystal is used for PET scans and at the higher coincident pair spectral energies will produce brighter scintillations inherently resulting in longer decay times. Because the PMT signals are processed as analog signals as soon as and while they are being produced, the invention inherently eliminates or minimizes the photon pile up effect resulting in fluorescence. However, the decay time of the pulse at the higher coincident pair energies, can itself contribute to fluorescence. Since the total energy of the pulse is reduced in baseline estimate circuit 44, the fluorescence attributed to overlapping tail portions with leading edge pulse portions is minimized.

The baseline corrected PMT pulse passes through a normal gamma camera SPECT detection circuit indicated by dash line envelope 50 in FIG. 5. SPECT detection circuit 50 includes an event detector 52 which typically includes a dv/dt circuit that senses the slope of the pulse signal's leading edge to make sure that a steep rise indicative of a scintillation event has occurred. The dv/dt circuit may be coupled with a maximum amplitude sensing circuit such as shown by curve 49 in FIG. 5. When event detector 52 detects a scintillation event, an integrator timing circuit 53 is actuated. Integrator timing circuit 53, in turn momentarily actuates, in effect, a switch 54 which momentarily establishes contact with an integrator 55. Integrator timing circuit 53 also controls the time during which integrator 55 integrates the PMT's analogue pulse signal to produce an intensity or z component signal which is sent to a multiplexor 58. Integrator timing circuit 53 also inputs to the motherboard or control and centroid calculator 60 the fact that event detector 52 has detected a specific scintillation event for a specific PMT 15. Control and centroid calculator 60 then determines, for the specific PMT which detected the scintillation event, a grouping or cluster or bundle of PMTs and for each PMT within the bundle, control and centroid calculator 60 causes integrator timing circuit 53 to close switch 54 so that integrator 55 integrates the intensity of each PMT pulse signal within the bundle. In the preferred embodiment, 18 PMTs adjacent that specific PMT which detected the scintillation event and the triggering PMT which caused the triggering pulse signal, are bundled (i.e. a total of 19 signals in the preferred embodiment) and their analogue signals are multiplexed by multiplexor 58 under control of control and centroid calculator 60 to, in turn, generate a string of 19 PMT analogue signals, each having an intensity or z component and an address or x,y position component corresponding to the center of each PMT in the bundle. The bundle string of 19 PMT pulse signals will subsequently be digitized, analyzed and corrected by digital signal processors. Generating the signals for the SPECT mode as just described is entirely conventional (except for the baseline correction circuit 42) and is used in SMV's gamma cameras.

When the gamma camera is to be used in a PET mode, additional circuits are activated. The timing signal, specifically the triggering timing signal H, is generated for the PMT triggering pulse by means of a constant fraction discriminator 63 and a zero crossing comparator 64 which in turn generates a triggering pulse indicated generally by reference numeral 65. (It is to be understood for discussion purposes that any triggering timing signal is designated "H" and when followed by the number "1" refers to the specific triggering signal generated by the first detector head and when followed by the number "2" refers to the specific triggering signal generated by the second detector head. The first in time signal of a matched pair could originate from either the first or the second detector head.) As is well known, a constant fraction discriminator delays the input pulse and a fraction of the undelayed input is subtracted from the pulse to produce a signal as shown by CFD curve 67. Zero crossing comparator 64 detects the zero crossing 68 of the constant fraction discriminator pulse to cause issuance of an output logic triggering pulse 65, i.e., H. It is commonly accepted that constant fraction discriminators produce the best time resolution of the PMT's pulse regardless of the pulse height (See Photomultiplier Handbook by Burle Industries. 1989 pages 98–99). Activation of constant fraction discriminator occurs by an arming signal shown by reference numeral 69 which occurs when the PMT's signal exceeds a predetermined voltage correlated to the spectral energy of the radiation. For PET studies, this voltage is set to correlate to the energy level attributed to Compton scattering of the coincident pair photons in the crystal. That energy level is also detected and triggers event detector 52. As schematically shown in FIG. 5, event detector 52 also provides the arming signal 69 to actuate constant fraction discriminator 63. Thus when SPECT detection circuit 50 detects a scintillation indicative of a potentially valid annihilation event, constant fraction discriminator 63 is armed or triggered and the same electrical pulse processed in SPECT detection circuit 50 is also converted into triggering timing signal H. Software, set by the operator to coincide with the spectral energy limits of the sensed radiation, controls triggering limits set by event detector 52.

It is contemplated that the gamma camera, when equipped with a thin lead collimator, can be used to simultaneously perform both PET and SPECT studies during one scan session. It is believed that dual imaging of different radioactive isotopes (now used in SPECT studies) will have particular benefit in cancer studies. However, until this invention it was not possible to perform such studies. Specifically, the gamma camera will collect data sufficient to generate a scintigram in a SPECT mode and then automatically switch to its PET scan mode to generate a PET image. While the images are not simultaneously produced, they only lag one another by the time it takes the gamma camera to gather the data to complete a SPECT or PET image. Since the PET and SPECT images are immediately sequentially generated very close in time to one another, the information obtained from the images will be useful in treating the cancer or other maladies. Automatic switching of the gamma camera from one mode to the other upon completion of a scan can be accomplished in any number of ways. One simple way of accomplishing this is through a switch 61 to each constant fraction discriminator 63 under the control of a multiplexor (not shown) in turn software actuated upon completion of data acquisitioning for any given scan. To distinguish between higher and lower energy photons, event detector 52 could optionally have higher and lower amplitude settings and is triggered in a SPECT study only when the pulse signal passes the lower amplitude or voltage setting but not the higher setting. In this manner FDG radiation will not adversely influence the SPECT study since most spectral energies of SPECT radiation is below the spectral energy of Compton scattered coincident pair radiation.

It is to be understood that all 58 PMT's in each detector head are continuously generating pulse signals, and as triggering pulse signals are detected, a stream of triggering timing signals are generated and directed to a timing signal multiplexor 70 under the control of control and centroid calculator 60 which in turn individually gates each signal to coincidence unit 20. Thus a stream of individual triggering timing signals H1, H2 for each detector head is continuously directed to coincidence unit 20 while the PMTs triggering pulse signal, along with a grouping of other related PMT pulse signals are bundled together and held by multiplexor 58 for processing. If the triggering timing signal from any one detector head is matched in coincidence unit 20 with a triggering timing signal from the other detected head thus establishing a valid annihilation event, then each of the matched pair of triggering timing signals, now a validated triggering timing signal, is returned to multiplexor 58 to gate or release the bundled PMT's pulse signals, which correspond to the validated triggering timing signal to the analog to digital processor. If the validated triggering timing signal does not return, control and centroid calculator 60 is advised of the fact by coincident unit 20 and simply discards the bundled PMT pulse signals corresponding to the unreturned triggering timing signal.

Figure 7:
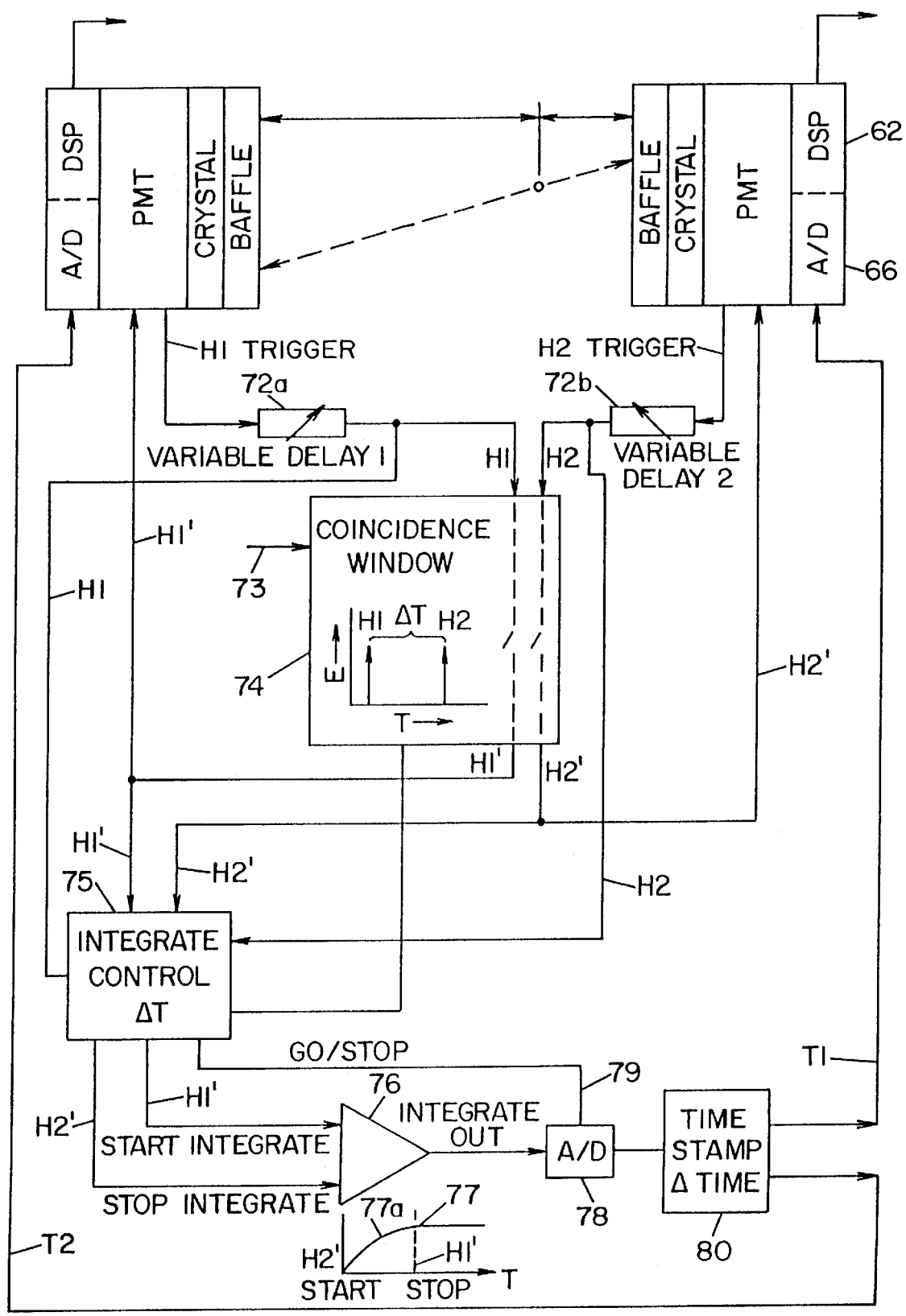
FIG. 7 is a general schematic block diagram showing in greater detail than that shown in FIG. 2 the coarse coincidence timing arrangement of the present invention.

Referring now to FIG. 7, where coincidence unit 20 is shown in greater detail than that illustrated in FIG. 4, each triggering timing signal H1, H2 passes through a variable delay 72a, 72b associated therewith. One of the variable delays 72a, 72b is set for a calibration lag time established when the gamma camera is calibrated as will be described further below. In addition, one of variable delays 72a, 72b is set to produce a conventional timing delay between triggering signals H1, H2. After passing through variable delays 72a, 72b triggering signals H1, H2 are processed through a coincidence window timing circuit 74 which is conventional. Coincidence window timing circuit 74 senses the time difference between the time it receives the first to arrive triggering signal, either H1 or H2, and the second to arrive triggering signal (H2 if H1 arrived first or H1 if H2 arrived first) and if the time difference is within a preset time window, the triggering signals are established as a matched set of validated triggering signals H1' and H2' indicative of a positron annihilation event and the validated signals are switched or gated through coincidence window circuit 74. The timing window for coincidence window timing circuit 74 is, like variable delays 72a, 72b, software set (as shown schematically by reference numeral 73) to equal the conventional time delay of the variable 72a or 72b (but not the calibration delay) plus some additional time delay, such as twenty nanoseconds. Thus, in the preferred embodiment, coincidence window circuit 74 determines that if triggering timing signals occur within 20 nanoseconds of one another they are valid events. This is a "coarse" determination of a positron annihilation event. Later, in the signal processor, a "fine" determination of events more likely to be "true" positron annihilation events will be made. If two triggering timing signals from opposite detector heads 12 do not occur within the coincidence timing circuit set time, the first in time triggering timing signal is discarded by coincidence timing circuit 74 (and control and centroid calculator 60 is told) which waits for the next successively generated triggering timing signal H1 or H2 to arrive to determine if a pair of triggering timing signals from opposing detecting heads 12 can be matched. The validated triggering signals H1' and H2', having successfully passing through coincidence timing circuit 74 are each then routed back to their respective timing multiplexor 58 to cause control and centroid calculator 60 to release the analog pulse signals of the bundled PMTs to analog to digital converters 66 for digitizing and further processing.

In addition to individually gating or releasing the corresponding bundled PMT pulse signals, validated triggering signals H1', H2' are also sent to an integrator control 75 which factors out the conventional time delay (but not the calibration delay) imposed on triggering signals H1, H2 by variable delays 72a, 72b and releases the first in time validated triggering timing signal to start an integrator 76 and the second in time validated triggering timing signal to stop integrator 76. This is best shown by integrator timing curve 77 in which the first validated triggering timing signal, assumed to be H1' for illustrative purposes, starts integrator 76 and the second validated triggering timing signal H2' stops the rise of integrator timing curve 77. Since integrator 76 is calculating the area under integrator timing curve 77, a go/stop signal 79 starting and stopping the integration by integrator 76 is developed by integrator control 75 from triggering timing signals H1, H2. Go/stop signal 79 is inputted to an analog to digital convertor 78 to develop a digitized signal indicative of the area under integrator timing curve 77 which is correlated only to the rise portion of integrator timing curve 77 (designated as 77a) which in turn is set by the start/stop validated triggering timing signals H1' and H2' as just described. The digital signal is then refined in a time stamp converter 80 to develop two time stamped digitized numbers (32 bits in the preferred embodiment) indicated as T1 and T2. The 32 bit timing signal then subsequently formed into the four 8 bit digitized signals discussed above in processor 33. In theory the timing numbers can be some absolute value, but in practice the first in time stamp signal T1 or T2 (resulting from the first in time validated triggering timing signal, H1' or H2'), is assigned a value of zero and the second in time timing signal T1 or T2 is assigned a digitized number indicative of the time delay between the validated triggering timing signals. Timing signals T1 and T2, as shown in FIGS. 3 and 4, are then assigned to each one's respective bundle of PMT pulse signals initially gathered for that scintillation event which is now established as a scintillation caused by two photons emitted as a result of a positron annihilation. Digitized timing signals identify each matched set of scintillations and the observed time difference between the two signals. In the preferred embodiment, each bundle of PMT pulse signals corresponding to the scintillation is assigned three 8 bit digitized time stamp signals. Alternatively, it is within the scope of the invention that each PMT pulse signal within the bundle can have assigned to it, as part of its digitized address, a digitized time stamp component.

Figure 8:
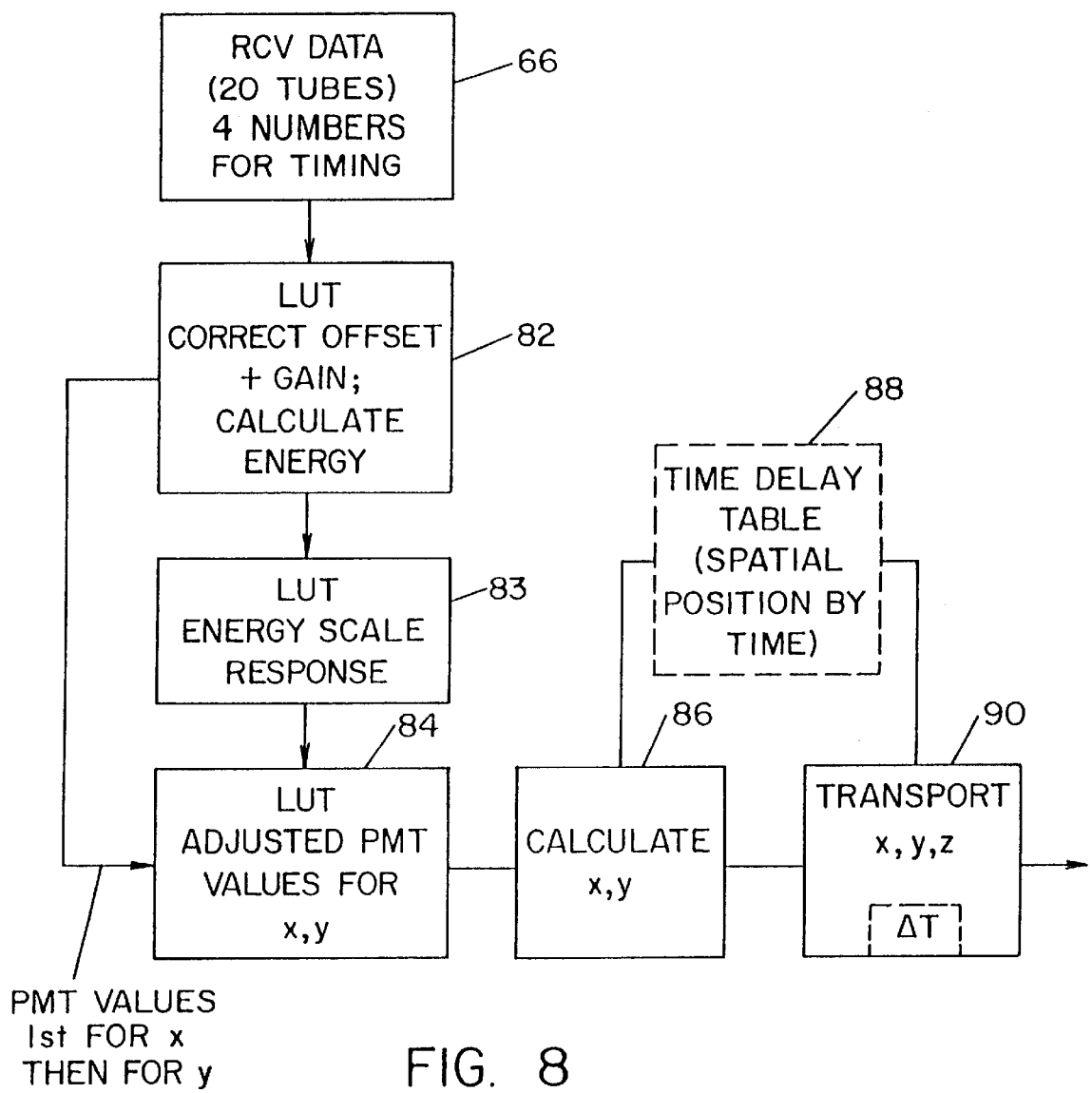
FIG. 8 is a schematic, flow chart of a portion of the digital signal processors used in the invention.

Referring now to FIG. 8, there is shown the digital signal processors used in the invention in block form and arranged in a flow chart manner. As is well known digital signal processors typically perform arithmetic calculations under the control of acquisition CPU 35 utilizing RAM and ROM with CPU 35 containing read only memory in the form of look up tables accessed by the digital signal processor for performing the desired calculations and will not be described in detail herein. Those skilled in the art understand that the look up tables stored in memory for a gamma camera contain correction values resulting from calculations applied by known algorithms to base signals generated by the gamma camera, usually established during camera calibration.

Those digital signal processors illustrated in FIG. 5 in solid block form are the same signal processors used by the assignee, SMV, in its conventional gamma camera for SPECT studies and the digital signal processors illustrated in dash block form are additional digital signal processors added by the invention to the conventional processing arrangement to account for PET studies. As discussed above, each validated event (determined by coincidence unit 20) has 19 PMT pulse signals. Each PMT digitized pulse signal has bits designating its energy and in addition there are four 8 bit digitized timing numbers for each bundle, with one 8 bit signal containing timing data and the other 8 bit signals containing synchronization information. Receptor digital signal processor 66 transmits the bundle to an offset correction digital signal processor 82 which accesses look up tables to correct the x and then the y positions of the digital numbers which, as modified, are sent, first by x position and then by y position to adjusted PMT digital signal processor 84. Adjusted PMT processor 84 reforms or regroups the x, y and signals and further corrects the x, y signals based on their two dimensional position by additional look up tables stored in memory. Offset correction processor 82 also calculates the intensity or z signal and transmits the z signals to an energy scale response digital signal processor 83. Energy scale processor 83 in turn accesses look up tables and adjusts the z signals to account for degradation of that signal which, when corrected, is sent to adjusted PMT processor 84 where each PMT's adjusted energy signal, z, and adjusted position signal x, y are grouped, further adjusted and then sent to calculator digital signal processor 86. Calculator processor 86 weights each of the 19 signals by intensity and then sums and averages the weighted signals (i.e., weighting) to arrive at one signal having a precisely calculated x,y position with a calculated intensity z. This signal when further corrected for energy and linearity is the conventional gamma signal used to develop a pixel of a scintigram in a SPECT study. Thus the processing arrangement illustrated in FIG. 8, to this point is conventional and corresponds to the digital signal processors set forth in processor 33 illustrated in FIG. 4.

Included with the corrected position and linearity signal is the timing signal T. Importantly timing signal T is also modified by a timing digital signal processor 88 based on the corrected x, y position of each scintillation event comprising a matched pair. Timing processor 88 uses look up tables generated from histograms developed during calibration which compares the time delay correction values stored for any LOR x, y pixel position with the actual time delay measured by integrator 76 in coincidence unit 20 and corrects the time value accordingly. This fine correction following the fast analog coarse correction forms one of the underpinnings of the invention. Those skilled in the art know that signal time variations as high as 20 nanoseconds can occur depending on the point at which the photon strikes the face plate of the photomultiplier and schemes have been proposed and implemented to account for the initial contact point on the PMT so that the coincidence timing arrangements in PET scanners can adequately distinguish such events. More significant than this is the timing variations inherent in the electronics and digital signal processors attributed to signal noise. In the invention the conventional gamma camera processing arrangement develops a precise x,y scintillation point (and not a point at the assumed center of a PMT otherwise functioning to calculate the LOR) and the timing signal for that point is then corrected by statistically validated data developed for that specific camera during calibration to account for all time variations including signal noise, PMT time variations, PMT scintillation points, etc.

Figure 9:
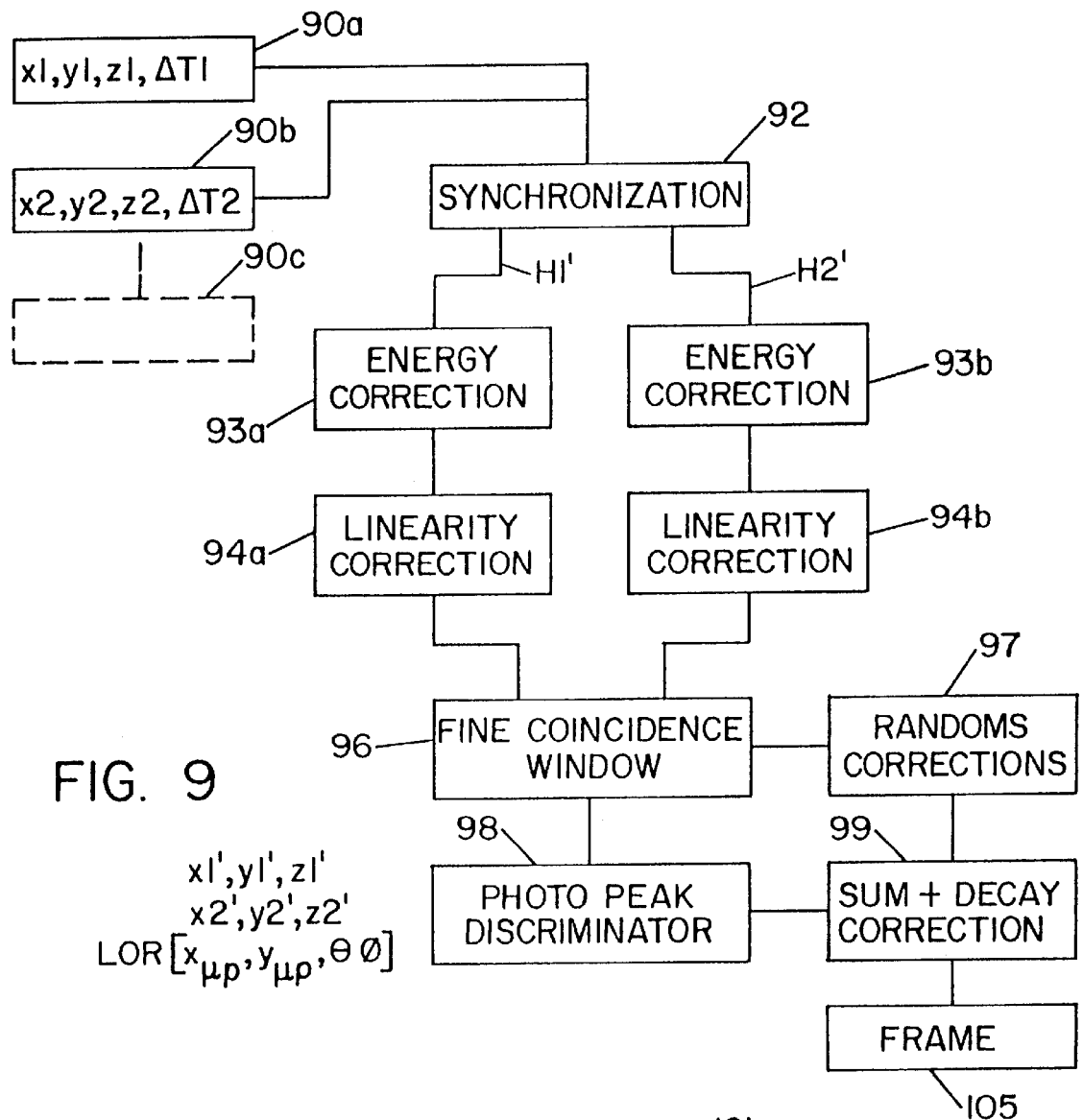
FIG. 9 is a schematic, flow chart, similar to FIG. 5, showing the digital signal processors for synchronizing and generating data to calculate LORs for PET studies.

Timing signal processor 88 transmits the corrected timing signal, T1' or T2', to a transport digital signal processor 90 which assimilates the corrected timing signal with the corrected position, x,y, and energy, z, signals for further processing by fine digital signal processors 36. Referring now to FIG. 9 which illustrates in greater detail digital signal processors 34, 36 shown in FIG. 4, the signals pass through a synchronization digital signal processor 92. As those skilled in the art know, because of delays in digital signal processors, the corrected data string transmitted by transport processor 90 for any given triggering PMT will not necessarily coincide with the data string for the matched triggering PMT. Synchronization processor 92 collects the data signals from transport processor 90 indicated by blocks 90a, 90b, etc, and using the time stamp signal (specifically the three 8 bit digitized synchronization signals) insures that the data signal blocks 90a and 90b, 90c and 90d, etc. are matched to coincide with the PMT triggering pulse signals which initially established the matched pair of validated triggering signals, H1' and H2'. Each matched data signal pair is then simultaneously processed and corrected for energy in energy signal digital signal processor 93a, 93b and linearity in linearity digital signal processor 94a, 94b. Energy signal digital processors 93 and linearity digital signal processors 94 are conventional energy and linearity processors used in a gamma camera in a SPECT study for conventional correction of the gamma signals for energy and linearity.

The refined and corrected signals are now passed to a fine coincidence window signal processor 96 which determines a corrected delay lag from the corrected time stamp signals which is compared to a shorter time lag (10 nanoseconds in the preferred embodiment) to determine whether the corrected signals are valid events indicative of a positron annihilation event. At this stage in the processing of the event, it must be again noted that the signals have been significantly refined from the original triggering signals generated by a single PMT. First the signals are no longer signals from two opposed PMT's 15 mounted on each detector head 12. The x,y signals are now precise pixel point signals generated from a weighted average of a bundle of PMT signals (thus generating a precise LOR) which have been further refined and corrected in accordance with conventional gamma processing techniques. Second, each timing signal T1, T2 has been corrected for that calculated pixel based on statistical sampling of data accumulated during calibration to account for delays in electronics, off center PMT scintillations, signal noise etc. The corrected position data establish a definitive path to calculate the LOR and the calibration of the camera establishes a statistically valid method of setting a time variation (e.g., standard deviation analysis) by which corrected timing signals can now be compared to accept or reject the matched signal set. If the corrected timing signals fall for the corrected positions within a close "time" time variation, fine coincidence processor 96 accepts the signals and if the time signals are outside the timing limits, fine coincidence processor rejects the signals and processes the next matched pair of data signals.

As noted, the time coincidence window signal processor 96 in the preferred embodiment sets a tighter time frame for checking the corrected signals to insure valid and not random event are generated and stored to develop, from a relatively small data base, accurate images. The data base can be relatively small because it is not distorted by the inclusion of false event data. In PET scanners, a larger database of sampled events results from the solid ring geometry than that produced by the detecting heads of a gamma camera. It is believed such larger database can expand the scope of the invention to include time of flight, especially because the electronics in a PET scanner are more expensive and, thus, more time sensitive than that used in a gamma camera. As noted from the earlier discussion above, from the actual time Ta which is that time now established by the corrected time stamp signals, T1', T2', it is possible to determine two positions on each LOR where a positron annihilation event occurred. Further, by noting which detector head was the first in time to generate the triggering time signal, it is possible to discard one of the two position signals. The corrected x,y positions fix two precise points between a known detector head position to allow calculation of the total time of flight for any LOR. While not used in the preferred embodiment, it is within the scope of the invention that the time stamp numbers can establish the actual time of flight for the precise points. Thus, it is now possible to obtain the precise point on the LOR where a positron annihilation event occurred. This calculation can easily be performed by a digital signal processor. It is thus believed that the exact point on the LOR where a positron annihilation event occurred can be established for a PET scanner using the invention because the electronic coarse coincident window in a PET scanner is "time", the database is large and the timing signals can be significantly tuned in the digital signal processors to discern the traditional nanosecond variations necessary for TOF (time of flight) measurements. The spatial resolution then of PET ring scanner employing the invention will be significantly advanced.

Figure 10:
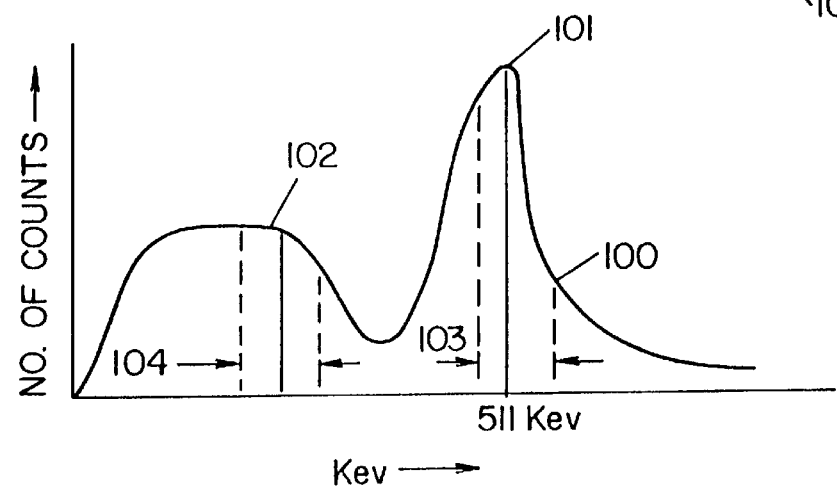
FIG. 10 is a graph depicting a histogram of positron annihilation scintillation events normally produced by any photomultiplier in the gamma camera.

Signals which pass fine coincidence processor 96 are sent to a photopeak discriminator digital signal processor 98. It is known from observation and it is generally known in the art, that any given PMT exposed to gamma rays produced by positron annihilations during a PET study will produce a variety of pulses having a varying range of energy and only some of which will have energies of 511 Kev. If the PMT pulse voltages or energies were stored in a multi-channel analyzer with channels set at incremental energies, a histogram having a curve 100 as shown in FIG. 10 would be developed. Histogram 100 has a sharp peak portion 101 corresponding to the 511 Kev energy of the photon resulting from the positron annihilation and a flatter peak portion 102 attributed to Compton scattering of the positron annihilation photon. The invention utilizes Compton scattered photons to increase its count rate to obtain count efficiencies approximating that of typical PET scanners. As discussed above, the two detector heads of the gamma camera cannot gather anywhere near the same number of annihilation events in a one dimensional plane inherently detected in the solid angle produced by the circumscribing rings in a conventional PET scanner. The invention assigns an energy range to the 511 Kev positron annihilation events indicated generally as 103 in FIG. 10 and a lower energy range to the detected photons which may have experienced Compton scattering in the crystal indicated generally as 104 in FIG. 7. Event detector 52 is set at lower energy range 104. When the invention is utilized for dual SPECT and PET imaging, thin collimator 11 will, of course, stop high angular Compton scattered rays produced in the body of the patient from coincident pair photons. Low angle Compton scattered rays in the patient body could pas through the collimator channels and be processed. However, low angular Compton deflections will not necessarily significantly distort the LOR. High energy angular 511 Kev photopeak photons will actually penetrate thin collimator 11 and be detected. High energy 511 Kev photopeak photons experiencing Compton scattering in crystal 31 will also be detected. The result is that images from both PET and SPECT studies with good resolution can be produced. When gamma camera 2 is used for PET studies only, a filter plate is used in place of collimator 11 as described in our patent application filed as of this date entitled "Prefilter Collimator for PET Gamma Camera". This invention uses the Compton scattered scintillations produced in crystal 31 to significantly increase the count rate by fine adjusted signal processors 36.

Photopeak discriminator processor 98 passes each matched signal set, if i) one signal 's z energy is within the 511 Kev positron annihilation energy range 103 and the other signal is also within the 511 Kev positron annihilation energy range 103; ii) if one signal is within the 511 Kev positron annihilation energy range 103 and the other signal is within the Compton scattered energy range 104 and iii) if the other signal is within the 511 Kev positron annihilation energy range 103 but the first signal is within the Compton energy range 104. If both signals are within the Compton energy range 104, the event is discarded. It should be recalled that constant fraction discriminator 63 was set to detect PMT events which had energies or voltages corresponding to the energies produced by a Compton scattered photon resulting from a positron annihilation event. It should also be noted that the z energy is not the energy produced by the original triggering PMT but a corrected energy indicative of a weighted average. It is also to be noted that the z correction in signal enhancement digital signal processors 36 utilize histograms developed during calibration such as shown in FIG. 10 which account or set the energy ranges 103, 104 for each specific PMT so that an accurate, weighted z energy signal indicative of true Compton events is obtained.

Photopeak discriminator 98 thus sends matched signals (occurring within a tight coincidence window of 10 nanoseconds) comprising position, x1', y1', and x2' and y2', to acquisition CPU 35 for framing and storing to disk 38 for subsequent tomographic construction in tomographic station 40. The tomographic reconstruction technique is not part of the present invention. The corrected x1',y1' and x2',y2' data establish a LOR in three dimensional space and from a large number of such LORs, it is believed one skilled in the art, can use any number of reconstruction techniques to construct an image of the body organ showing FDG concentrations therein. The corrected positron signals X1', y1' and x2', y2' have been validated to be true positron annihilation events by corrected timing signals passing within a tight coincident window and having corrected energies verified to match a positron.

There are two important corrections made to the LOR's prior to framing which are diagrammatically shown in FIG. 9. When the corrected signals are finally processed by photopeak discriminator 98, each LOR has been refined and corrected in the manner described to produced a validated LOR signal. The invention further processes and removes the for LOR signals by means of a random event processor 97 "noise" attributed to random events which pass through both coarse coincident window 74 and fine coincidence window 96 and adversely affects the image resolution of the camera.

This may best be explained by reference to the histogram illustrated in FIG. 10A. It is to be understood that each LOR signal is essentially histogrammed into pixel analyzers making up projection planes as will be explained with reference to FIG. 11 below.

Figure 10A:
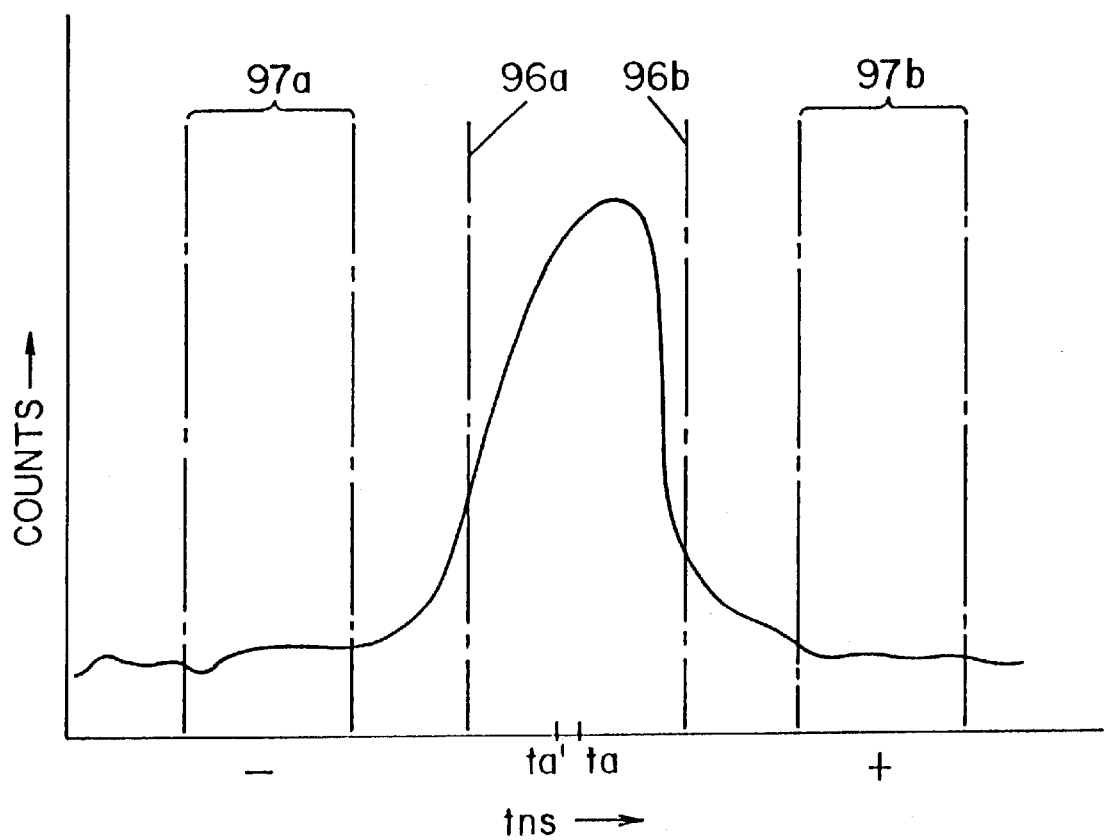
FIG. 10a is a histogram similar to FIG. 10 depicting the counts passing through the coarse coincident window and showing random events.

The histogram of FIG. 10A may be viewed as such an analyzer but one which contains all the data of matched triggering timing signals which passed through coarse coincidence window 74 for a given pixel of a projection plane. The curve shown in FIG. 10a plots the time of the timing signals on the x-axis and the number of counts observed for any given time increment on the y-axis. Fine coincidence window 96, shown by dot-dash lines 96a, 96b, results in a discard of the timing signals indicative of random events occurring on either side of fine coincidence window 96. It is obvious from a study of FIG. 10a that random events are also present within fine coincidence window 96. Rather than simply discard the random events, this invention histograms the random events, samples the data and adjusts the fine coincidence window events accordingly. It is significant to note that the adjustment is being done on a "pixel" basis from actual data obtained during the scan and is not based on a mathematical technique which produces an adjustment universally made to all the signals.

In the preferred embodiment, a sample of random events is averaged over a time span 97a occurring before fine coincidence window 96 and over a time span 97b (analogous to "bandwidth") occurring after fine coincident window. The random events occurring in time spans 97a, 97b are summed and added on a plus/minus basis to arrive at a difference signal which is applied to the count of validated events occurring within fine coincidence window 96. While not used in the preferred embodiment, those skilled in the art will recognize that the random events can be weighted and the weighted sum of the random events used to adjust the actual time of flight measurements. That is, if the invention were used to obtain time of flight measurements, the counts occurring within fine coincidence window 96 would be weighted to establish a time of flight, shown as $t_a$ and the weighted random events would be used to adjust the time of flight to a faster or slower time $t_a$. Thus a basis is provided in the invention, based on actual measurements, to adjust the validated photon annihilation events for the signals produced by the PMTs, on an individual by individual PMT basis, to accurately account for the influence of random event signals.

As noted framing processor 105 histograms a large number of planes, each of which in the preferred embodiment has a 64×64 matrix or pixel resolution, which are stored onto disk 38 for subsequent reconstruction in tomographic station 40. Generally, reconstruction typically utilizes algorithms to develop filtered backprojections to depict the origin of the rays in image form. Typically reconstruction techniques or algorithms by which the techniques are performed, are classified as either parallel beam, cone beam or fan beam reconstructions. Generally, PET scanners use either 2-D or 3-D parallel filtered backprojections to develop the image. In this invention, the reconstruction technique preferably used in tomographic station 40 is described as orthogonal plane filtered backprojections. Other filtered backprojection techniques can be employed.

Figure 11:
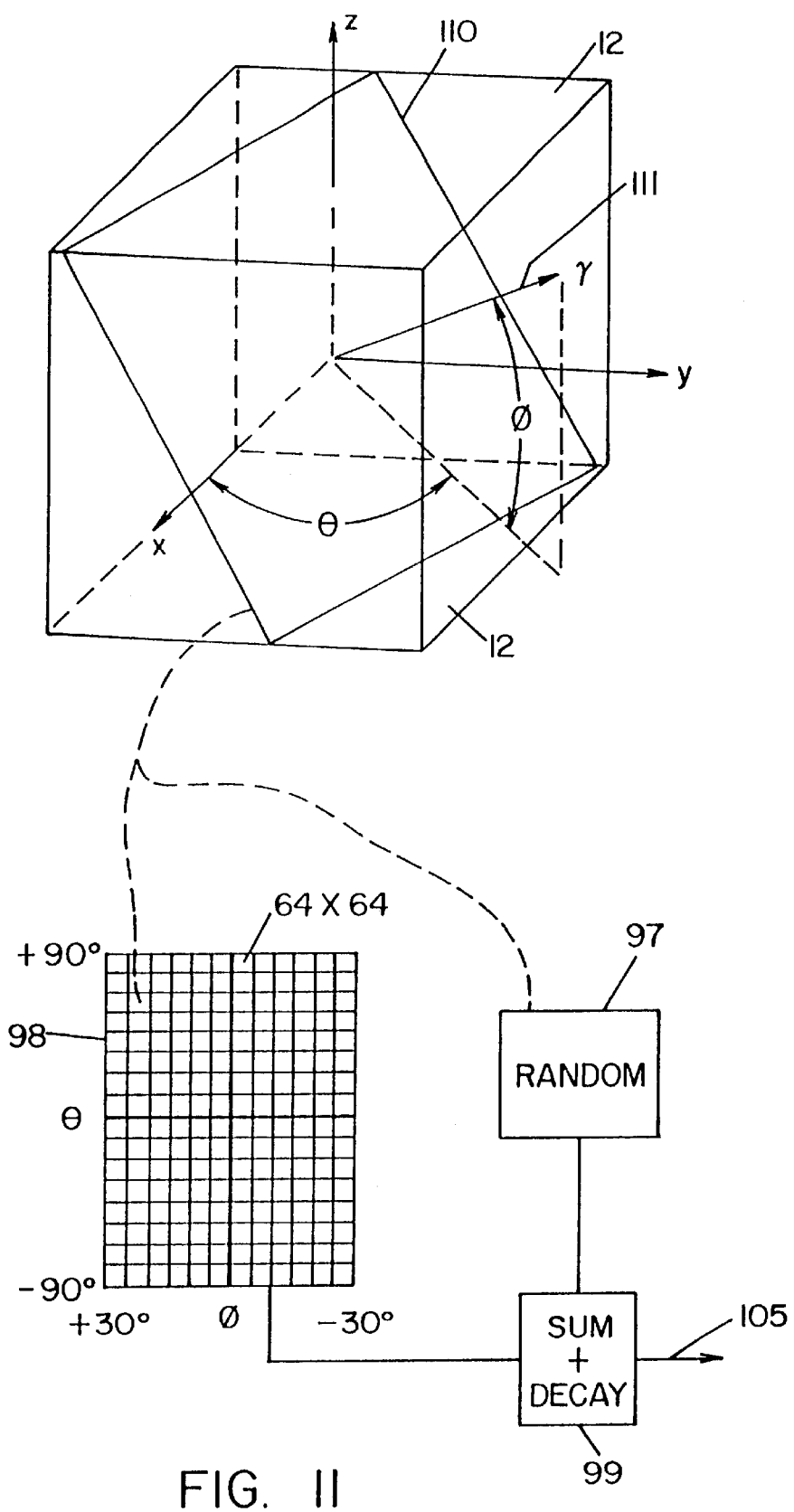
FIG. 11 is a three dimensional pictorial representation of an LOR.

In the preferred embodiment, as best shown in FIG. 11, a line of response, LOR, 111 extends in three dimensional space, x,y,z, between the two opposing detector heads 12. A plane 110 perpendicular to any given LOR 111 demonstrates the plane angle theta, $\theta$, made with respect to the x,y axis and the plane angle phi, $\phi$, made with respect to the z axis for any given plane 110. Each plane 110 has a 64×64 matrix or pixel array establishing a fine grid which precisely locates the point or pixel when any LOR 111 intersects any given plane 110. It is of course well known that a large number of LORs are being generated by the digital signal processors and acquisition CPU 35 is in fact histogramming the intersection points of each LOR with any given plane 110 on a pixel by pixel basis. Further the intersection points of the LORs with any given plane 110 forms a matrix of points, each point having a histogrammed value, which are framed and stored at disk 38 for subsequent tomographic reconstruction.

In accordance with the preferred embodiment of the invention, 60 planes or slices 110 extending between detector heads 12 are incrementally taken along an included theta angle of 180° (+90° to −90°) and 20 planes or slices 120 extending between detector heads 12 over an included phi angle of 60° (+30° to −30°) resulting in a plane grid or a matrix in a 60×20 array. The [60×20] matrix array can be viewed as a number of voxel planes filling the space between the detector heads 12. The validated coincidence signals generated after correction and after passing through photopeak discriminator 98 are basically in the form of $x_{\mu p}$, $y_{\mu p}$, $\theta$, $\phi$ and this signal will be stored in several planes at various x,y positions correlated to the path (establish by $\theta,\phi$) of each LOR 111 relative to detector heads 12. This matrix is schematically shown for the signals when corrected by photopeak discriminator 98. As the LOR signals are generated each pixel in each plane in the matrix becomes histogrammed with an intensity corresponding to the count number. Similarly a 60×20 array of projections are constructed from rejected random events for each pixel by random processor 97 as described above. The plane projections resulting from photopeak discriminator 98, on a pixel by pixel basis, are modified by the random event processor 97 and further modified by decay processor 97 to produce frames of the projections stored, in the preferred embodiment onto disks 38.

Figure 12:
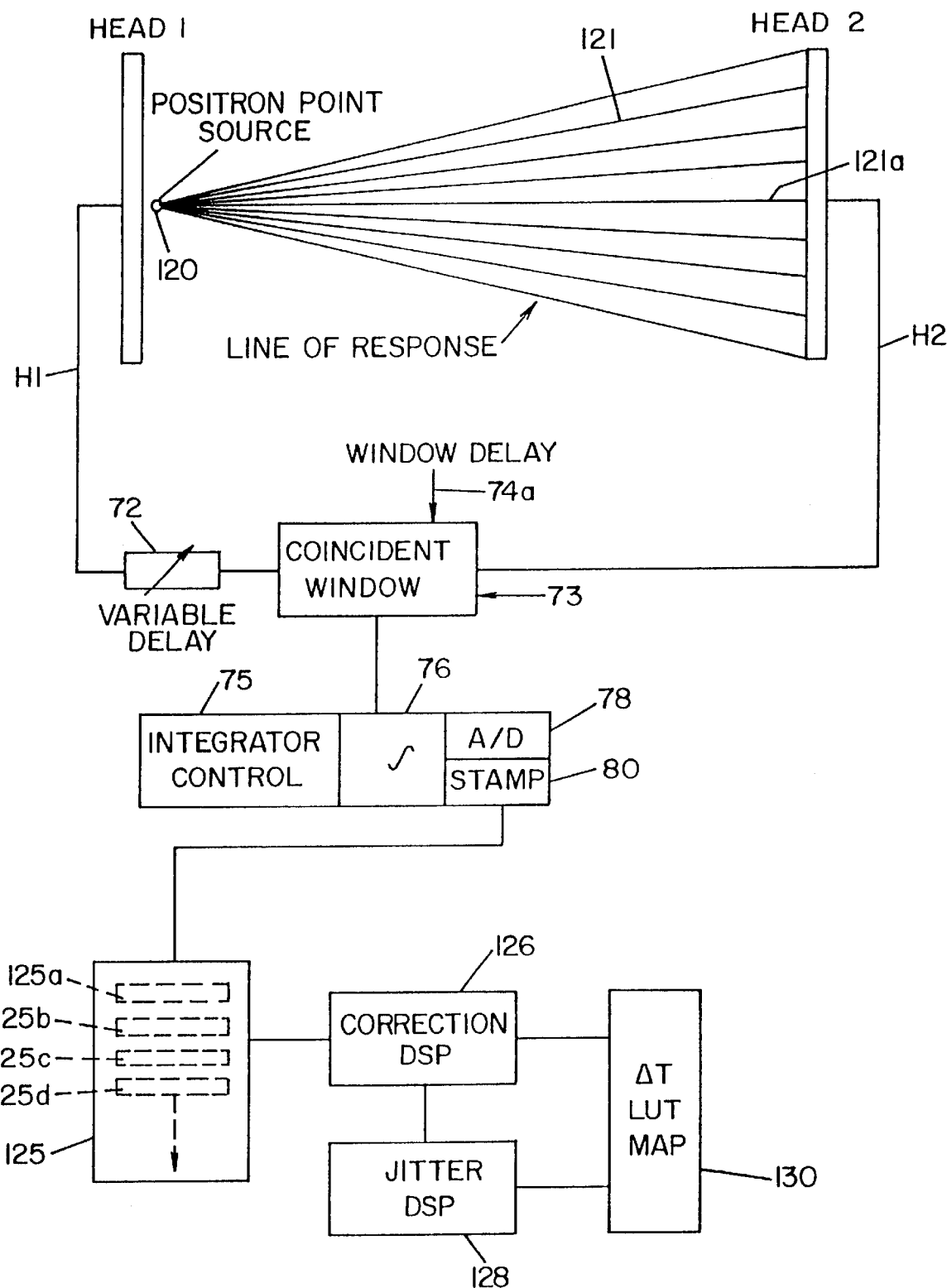
FIG. 12 is a pictorial representation of the arrangement used to calibrate the gamma camera for PET studies.

Referring now to FIG. 12, there is shown a schematic representation of the calibration arrangement used for the gamma camera. Those skilled in the art will recognize that the arrangement described in FIG. 12 is not limited to a gamma camera but can also be used for calibration of conventional PET scanners.

Generally, the calibration process is a two step process. First the detectors of one of the camera's detector heads are flooded with a uniform source of radiation resulting from a point source of a positron emitting radioisotope 120, such as FDG (F18) which is placed over the center of, preferably, the center PMT on the camera's detector head opposite the flooded detector head. A short delay is introduced to the point source and the triggering signals from the point source PMT and triggering signals from the PMTs are gated through a coincidence window and their time lag recorded. The delay time is subtracted from the recorded lag time to arrive at a flight time which is stored in an appropriate multi-channel analyzer for that triggering PMT. Histograms of the time delays are eventually formed for all the pixel points corresponding to the face of those PMTs on the flooded detector head and those histograms in turn provide the basis for forming a mean time delay map of the entire area of the flooded detector head to permit a time correction signal to be applied to any pixel or point through which a LOR extends. In the second step, the positron point source is then moved to the opposite detector head and the detector head initially containing the point source is flooded with uniform radiation. The process is repeated and the second detector head has a time correction map plotted for it as was done for the first detector head. The histogram for the same LOR between the centermost PMT and the point source when the point source is on the first detector head is then compared to the histogram constructed for the LOR between the centermost PMT and the point source when the point source is switched to the second detector head. In theory the histograms should be identical but they are not because of delays in the triggering or initial actuation of the electronics. The electronic triggering delay is now quantified and the camera electronics adjusted accordingly.

The apparatus of the gamma camera disclosed above is utilized to perform calibration as best shown in FIG. 12. A point source of radiation 120 is placed over the center of the centermost PMT 15 in one of the detector heads. Point source 120 develops many LORs 121 which uniformly flood the PMTs on the opposite detector head. Triggering timing signals H2 are developed by all PMTs in the flooded detector head while a triggering timing signal H1 is developed only for the center PMT where point source 120 is placed. (Positron radiation point source 120 could be placed over any PMT in the detector head but the centermost PMT is preferred.) Variable delay 72 for the point source detector head is set at a very short delay, about four nanoseconds. Timing or gating signal 74a for coincident window 74 is similarly set by software control 73 to a tight window of about 8 nanoseconds. Matched sets of triggering timing signals H2', H1' are then processed through integrator control 75, integrator 76, analog to digital converter 78 and time stamping processor 80 to develop matched timing signals T1, T2 as explained above with reference to FIG. 4. (Note that the camera electronics actually used to generate the triggering timing signal and triggering pulse signal in camera operation are used to establish the calibration data and the calibration data includes events detected as Compton scattered events in detector 52.) Since the first to occur time signal is stamped at zero, the later arriving timing signal contains the time lag of each matched pair of timing signals. The timing signal containing the timing lag is stored in a data bank 125 containing a multi-channel analyzer 125a, 125b, 125c, etc. for each PMT 15 in detector head 12. Each channel in each multi-channel analyzer 125a, 125b, etc. is set for some time increment range and the timing signals are stored as counts in each channel until any two or three adjacent channels are filled or filled to some percentage of an adjacent channel. Thus, each multi-channel analyzer builds a histogram of time lag data developed for each PMT of the flooded head. When all multi-channel analyzers 125a, b, etc. have been filled positron point source radiation 120 is moved to the other detector head and the process repeated.

Correction signal processors 126 read out each multichannel analyzer 125a, 125b, 125c, etc., and develop a correction time for each PMT (corrected to discrete pixel position) in the detector head. The corrections include i) reducing the data by the delay introduced in variable delay 72 (4 nanoseconds in the preferred embodiment) ii) obtaining an average or in the preferred embodiment, a mean time delay for each PMT by using one or more known statistical sampling techniques such as algorithms establishing form fitting curves, or sampling and averaging adjacent channels based on their count number etc., and iii) subtracting from the time lag established in (ii) the calculated time-of-flight for the LOR leading to the analyzed PMT based on a positron annihilation occurring at the point source 120. An averaged mean delay time for each PMT is obtained in correction processor 126 and the 58 PMT signals are mapped into an x,y pixel grid for any pixel point on the detector head according to conventional techniques and stored in a map look up table 130. That is, the PMT signals stored in each channel results from uniform radiation over the entire face of the PMT. The pixel mapping uses known algorithms based on calculated LORs to the point source radiation to store the mean time delay data on a pixel grid. A similar look up table is developed for the second head. Thus, map look up table 130 will generate a time delay for any x,y pixel position on a detector head. Look up table 130 is accessed by time delay processor 88 which subtracts the time, for the corrected x,y position, stored in map look up table from the time represented by time signal T1, T2. Again, the first in time timing signal is zero and when corrected with the bundled signals will have a negative number. When the bundled signals are matched in synchronization processor 92, a corrected time lag will now be calculated when the signals are subtracted. Thus, the timing signal for any one specific positron annihilation event is adjusted for an average electronic delay. This may or may not coincide with the actual delay for any specific event, but because the gamma camera samples a large number of LORs the time delay resulting from the sample is believed, as discussed above, to be surprisingly close to the actual delay results.

It is believed this calibration technique when applied to a PET ring scanner having relatively sophisticated and expensive circuitry will, in fact, generate accurate time-of-flight measurements.

It should be noted that when positron point source radiation is applied to the initially flooded detected array, data for only one common LOR 121a, the LOR extending between the center PMTs on each head will be generated. When the multi channel analyzers 125 for LOR 121a are analyzed, the time delays will not be equal. That is, the time delay obtained along LOR 121a when positron point source 120 is on one detector will not be the same as the time delay obtained for LOR 121a when positron point source 120 is on the other detector head. The difference is attributed to the delay in initially triggering the electronics (or jitter in the triggering of the electronics during the pulse signal) and determined by trigger processor 128 which, in turn, provides an adjustment to one of variable delays 72 when the gamma camera is operating.

The calibration arrangement forms an important underpinning which the invention utilizes in its processing arrangement to produce superior PET studies. First the calibration arrangement allows for adjustment in the electronics of the camera to account for electronic trigger delay by establishing a setting for one of the variable delays, 72a or 72b and thus provides for improved coarse determination of a positron annihilation event as established by the coincidence timing unit 20. (There must be two variable delays because it is not known which head will produce the greater trigger delay.) Second, the calibration arrangement allows for software calibration and correction of the "fine" coincident window time and does so in an arrangement where the mapping technique permits the correction to apply to a point or pixel position defining the LOR. Third the calibration arrangement inherently applies a method which develops a set of corrections unique to that specific camera which is calibrated and thus can be used as a performance verification tool to readjust the camera over long periods of time thereby accounting for variations in the electronic processing components which will inevitably occur over time and improving camera reliability. However, the most important aspect of the invention attributed to the calibration arrangement is the improvement in contrast resolution of the images. When the timing correction table is applied to the "fine" timing correction of the matched signals, the true coincidence window time, in fact, is actually reduced from about 100 nanoseconds to about 10 nanoseconds. This reduction, of one order of magnitude, dramatically increases the ratio of the camera processing true coincident events to random coincident events and significantly improves the contrast and spatial resolution of the resulting images.

As noted, the coincidence window calibration process is not necessarily limited to gamma cameras having area detector heads. If applied to ring PET scanner, the positron radiation point source would be fitted at the center of a given PMT and those PMTs extending about a diametrically opposed solid angle of either about 180° (for a 2 step process) or 90° (for a four step process) would be subjected to a uniform flood of radiation. Timing signals would be generated for the flooded group of PMTs, refined as discussed above and stored in opposite look up tables. The point source and grouping would then be swapped and the process repeated. Additionally, the timing data for the identical outer LORs would be compared to provide the calibration for trigger jitter.

The invention has been described with reference to a preferred embodiment. Obviously, modifications and alterations will suggest themselves to those skilled in the art upon reading and understanding the Detailed Description. It is intended to include all such modifications and alterations insofar as they come within the scope of the present invention.

Having thus defined the invention, it is claimed:

1. A gamma camera comprising:

detectors located proximate a patient, said detectors detecting scintillation events representative of emissions from the patient;

a coincident unit receiving event signals associated with said scintillation events, said coincident unit forming matched pairs based on said event signals, said matched pairs corresponding to scintillation events sensed by a pair of detectors situated on opposite sides of said patient that occur within a given time of one another, each matched pair including information indicative of a time difference between associated scintillation events;

a processor determining a corrected position of each scintillation event from a plurality of detectors detecting simultaneous scintillation events adjacent each detector in said matched pair; and a processor correcting time difference for matched pairs based on said corrected position of said scintillation events, thereby providing response information capable of use with emission imaging.

2. A method of operating a gamma camera, the method comprising:

detecting scintillation events representative of emissions from a patient by detectors positioned on opposite sides of said patient;

generating event signals associated with said scintillation events;

forming matched pairs based on said event signals, said matched pairs corresponding to pairs of scintillation events that are detected by a pair of opposed detectors and that occur within a given time of one another, each matched pair including information indicative of a time difference between associated scintillation events;

determining a corrected position of each scintillation event from a plurality of simultaneous scintillation events detected by a plurality of detectors adjacent each opposed detector of said matched pair; and correcting time differences for said matched pairs based on said corrected position of said scintillation events, thereby providing response information capable of use with emission imaging.

* * * * *